United States Patent [19]
Isaka et al.

[11] Patent Number: 5,830,902
[45] Date of Patent: Nov. 3, 1998

[54] QUINUCLIDINE DERIVATIVE HAVING TRICYCLIC HETERO CONDENSED RING

[75] Inventors: Masahiko Isaka, Bangkok, Thailand; Tsukasa Ishihara, Ibaraki, Japan; Koyo Matsuda, Ibaraki, Japan; Hirotoshi Kakuta, Ibaraki, Japan; Hiroshi Moritani, Ibaraki, Japan

[73] Assignee: Yamanouchi Pharmaceutical Co., Ltd., Tokyo, Japan

[21] Appl. No.: 894,549

[22] PCT Filed: Mar. 1, 1996

[86] PCT No.: PCT/JP96/00491

§ 371 Date: Aug. 21, 1997

§ 102(e) Date: Aug. 21, 1997

[87] PCT Pub. No.: WO96/26938

PCT Pub. Date: Sep. 6, 1996

[30] Foreign Application Priority Data

Mar. 2, 1995 [JP] Japan ................................. 7-043325
May 24, 1995 [JP] Japan ................................. 7-125050

[51] Int. Cl.⁶ ................... A16K 31/435; C07D 401/12; C07D 413/12; C07D 417/12

[52] U.S. Cl. ................... 514/305; 514/226.2; 514/230.5; 544/35; 544/37; 544/38; 544/102; 546/133; 546/137

[58] Field of Search .................... 546/133, 137; 544/35, 37, 38, 102; 514/226.2, 230.5, 305

[56] References Cited

U.S. PATENT DOCUMENTS 5,654,315   8/1997   Brown et al. ........................... 514/305

FOREIGN PATENT DOCUMENTS

93/15073   8/1993   WIPO .

*Primary Examiner*—Bernard Dentz
*Attorney, Agent, or Firm*—Burgess, Ryan & Wayne

[57] ABSTRACT

A quinuclidine derivative represented by the following general formula (I), a pharmaceutically acceptable salt thereof, a hydrate thereof or a solvate thereof, which has strong squalene synthase inhibiting activity and is useful as a cholesterol lowering agent without causing side effects.

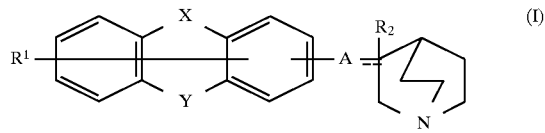

(Symbols in the formula represent the following meanings;

$R_1$: a hydrogen atom, a halogen atom or a lower alkyl group, $R_2$: a hydrogen atom, a hydroxyl group or a lower alkoxy group, ... : a single bond or a double bond, with the proviso that $R_2$ does not exist when ... is a double bond, X and Y: the same or different from each other and each represents a bond, an oxygen atom (—O—), a carbonyl group (—CO—), a group represented by the formula —S(O)$_p$— or a group represented by the formula —NR$_3$—, p: 0, 1 or 2, $R_3$: a hydrogen atom or a lower alkyl group which may have a substituent, A: a saturated or unsaturated lower alkylene group, a group of the formula —(CH$_2$)$_m$Z(CH$_2$)$_n$— or a group of the formula —(CH$_2$)$_m$Z(CH$_2$)$_n$CR$_4$=, Z: an oxygen atom (—O—), a group of the formula —S(O)$_q$—, a carbonyl group (—CO—) or a group of the formula —NR$_5$—, $R_4$: a hydrogen atom, a halogen atom or a lower alkyl group, $R_5$: a hydrogen atom or a lower alkyl group, m and n: the same or different from each other and each is 0 or an integer of 1 to 5, m+n: an integer of 1 to 5 q: 0, 1 or 2, with the proviso that, when either one of X and Y is a bond, A is a group represented by the formula —(CH$_2$)$_m$Z(CH$_2$)$_n$CR$_4$=.)

19 Claims, No Drawings

QUINUCLIDINE DERIVATIVE HAVING TRICYCLIC HETERO CONDENSED RING

This application is a 371 of PCT/JP96/00491 filed Mar. 1, 1996.

TECHNICAL FIELD

This invention relates to a novel quinuclidine derivative having a tricyclic hetero condensed ring, a salt thereof, a hydrate thereof or a solvate thereof, which has a squalene synthase inhibiting action, and to a squalene synthase inhibitor which contains the compound as the active ingredient.

BACKGROUND ART

It is known that arteriosclerosis induces various diseases. For example, ischemic heart diseases induced by coronary arteriosclerosis have the highest mortality rate next to cancer in Japan, and it is known that cerebral infarction induced by cerebral arteriosclerosis is accompanied by serious secondary diseases such as difficulty of moving, dementia and the like. In addition, since these various diseases induced by arteriosclerosis have been increasing with the increase in aged population and the changes in the dietary life into European and American styles, great concern has been directed toward the development of on effective therapeutic agent.

Increase in the blood cholesterol level is considered important as a main causal factor of arteriosclerosis which is a degenerative disease of the artery. Increase in the blood cholesterol firstly causes increase in blood lipid level and deposition of lipid on the inner membrane of large blood vessel, and the range and degree of these phenomena increase with the advance in years, finally causing ischemic heart diseases such as myocardial infarction, angina pectoris and the like, cerebral arteriosclerotic diseases such as cerebral infarction and the like and clinical symptoms such as aneurysm and the like. In consequence, it is considered that inhibition of the increase in blood cholesterol and its reduction to normal level are markedly effective for the treatment or prevention of the aforementioned various diseases caused by arteriosclerosis.

From the above point of view, attempts have been made to develop various hyperlipemia-treating agents. Cholesterol in the living body is provided as a portion absorbed from food and another portion synthesized in the living body and excreted mainly as bile acid. In the case of humans, 50% or more of the total cholesterol is originated from de novo synthesis in the living body. In consequence, inhibition of an enzyme which is concerned in the biosynthesis of cholesterol seems to be effective in treating hyperlipemia, and lovastatin, simvastatin and pravastatin are now clinically used as inhibitors for such an enzyme [cf. A. W. Alberts et al., *Proc. Natl. Acad. Sci.*, vol. 77, p. 3957 (1980); Tsujita et al., *Biochim. Biophs. Acta*, vol. 877, p. 50 (1986); and Koga et al., *Biochim. Biophs. Acta*, vol. 1045, p. 115 (1990)].

However; the aforementioned known inhibitors aim at 3-hydroxymethylglutaryl coenzyme A reductase (hereinafter, to be referred to as HMG-CoA reductase) as the target enzyme, and this enzyme is located at a relatively early stage of the cholesterol biosynthesis system. Accordingly, it is possible that inhibition of the enzyme by the administration of the aforementioned agents may also induce inhibition of the synthesis of other important metabolic products such as dolichol, ubiquinone, isopentenyl tRNA, p21Ras, low molecular weight G protein and the like which are concerned in intracellular information transfer and cell growth (cf. *Trends Biochem. Soc.*, vol. 4, p. 230 (1993), *Cell*, vol. 65, p. 1 (1991)).

In fact, it is known that growth of cells does not occur due to interruption of the cell cycle when an HMG-CoA reductase inhibitor is added to the cultured cells (Sakakibara et al., *Protein, Nucleic Acid and Enzyme*, vol. 39, p. 1508 (1994)), and side effects such as hepatic cytotoxicity and myopathy have also been observed.

In addition, it has been reported that triparanol known as the inhibitor of an enzyme located at a downstream stage of the cholesterol biosynthesis system accumulates desmosterol which causes the cataracts.

In consequence, an inhibitor which targets squalene synthase, an enzyme positioned at a stage after branching into physiologically important metabolic products and before formation of lanosterol that becomes a causal substance for arteriosclerosis, will provide a cholesterol biosynthesis inhibitor which has more higher safety and does not cause inhibition of the synthesis of other metabolites and does not cause accumulation of toxic substances in the living body.

Also, the activities of HMG-CoA reductase and squalene synthase are both down-regulated by sterol [Faust, J. R., Goldstein, J. L. and Brown, M. S., *Proc. Nat. Acad. Sci. USA*, vol. 76, pp. 5018–5022 (1979)]. In the case-of HMG-CoA reductase, considerable induction of enzyme activity occurs when supply of sterol is blocked by inhibiting its activity, thus inevitably requiring increase of the dosage, while such an induction is small in the case of squalene synthase which therefore can bear efficient reduction of blood cholesterol level without increasing its dosage.

Several compounds have been known as such inhibitors of squalene synthase. For example, it is known that certain quinuclidine derivatives disclosed in international patent publications WO 92/15579, WO 93/13096, WO 93/09115 and WO 95/31458 have squalene synthase inhibiting action and cholesterol biosynthesis inhibiting action. All of these compounds are quinuclidine derivatives having two independents rings such as biphenyl group and the like as substituents.

On the other hand, WO 93/15073 shows compounds by a general formula in which an azabicyclo ring such as of quinuclidine or the like is linked to an aromatic ring or hetero aromatic ring via an alkylene chain which may have one hetero atom or unsaturated bond. Of these compounds, however, only compounds having dibenzofuran are illustratively disclosed as compounds which have hetero aromatic rings, particularly tricyclic hetero condensed rings, and nothing is illustratively disclosed or suggested about other compounds having tricyclic hetero condensed rings. That is, only three compounds of

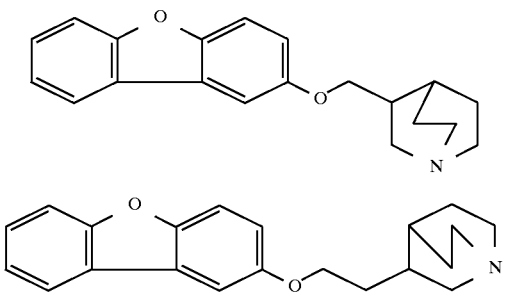

-continued

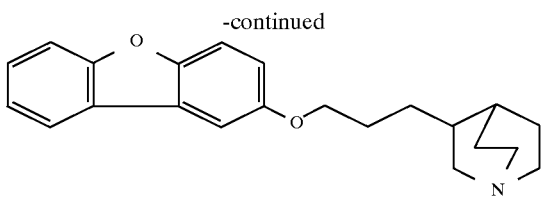

are illustratively disclosed. In addition, their use is calcium channel antagonist, and nothing is disclosed or suggested about the cholesterol biosynthesis inhibiting action or squalene synthase inhibiting action.

As described in the foregoing, various studies have been made, but development of an excellent squalene synthase inhibitor is still an important subject from clinical point of view.

DISCLOSURE OF THE INVENTION

In carrying out a study to find a compound having squalene synthase inhibiting action, the inventors of the present invention have conducted a synthesis study with a focus of a quinuclidine derivative which has a tricyclic hetero condensed ring. We have conducted the synthesis study also with a focus on the bonding moiety between the quinuclidine and the tricyclic hetero condensed ring. As the result, it was found that a novel quinuclidine derivative having a specified tricyclic hetero condensed ring, represented by the following general formula (I), has a strong squalene synthase inhibiting action, resulting in the accomplishment of the present invention. It was also found that a compound represented by the following general formula (I) in which the bonding moiety between the quinuclidine and the tricyclic hetero condensed ring is a specified carbon chain ($-(CH_2)_mZ(CH_2)_nCR_4=$) having a double bond on its terminal has a strong squalene synthase inhibiting action.

Thus, the object of the present invention is to provide cholesterol biosynthesis inhibitors, particularly a squalene synthase inhibitor represented by the following general formula (I) whose chemical structure is different from those of the prior art compounds and which is excellent in terms of markedly reduced side effects and higher safety, for example, showing less danger of inhibiting the synthesis of other metabolites and accumulating toxic substances in the living body.

In addition, the object of the present invention is to provide a medicine having squalene synthase inhibiting activity, which contains a novel quinuclidine derivative having a tricyclic hetero condensed ring, represented by the following general formula (I), a pharmaceutically acceptable salt thereof, a hydrate thereof or a solvate thereof as its active ingredient, or a pharmaceutical composition which comprises the compound (I) of the present invention, a pharmaceutically acceptable salt thereof, a hydrate thereof or a solvate thereof and a pharmaceutically acceptable carrier.

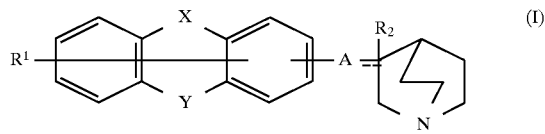

(Symbols in the formula have the following meanings;
$R_1$: a hydrogen atom, a halogen atom or a lower alkyl group,
$R_2$: a hydrogen atom, a hydroxyl group or a lower alkoxy group, ... : a single bond or a double bond,
with the proviso that $R_2$ does not exist when ... is a double bond,
X and Y: the same or different from each other and each represents a bond, an oxygen atom (—O—), a carbonyl group (—CO—), a group represented by the formula $-S(O)_p-$ or a group represented by the formula $-NR_3-$,
p: 0, 1 or 2,
$R_3$: a hydrogen atom or a lower alkyl group which may have a substituent,
A: a saturated or unsaturated lower alkylene group, a group represented by the formula $-(CH_2)_mZ(CH_2)_n-$ or a group represented by the formula $-(CH_2)_mZ(CH_2)_nCR_4=$,
Z: an oxygen atom (—O—), a group represented by the formula $-S(O)_q-$, a carbonyl group (—CO—) or a group represented by the formula $-NR_5-$,
$R_4$: a hydrogen atom, a halogen atom or a lower alkyl group,
$R_5$: a hydrogen atom or a lower alkyl group,
m and n: the same or different from each other and each is 0 or an integer of 1 to 5,
m+n: an integer of 1 to 5, and
q: 0, 1 or 2,
with the proviso that A is a group represented by the formula $-(CH_2)_mZ(CH_2)_nCR_4=$ when either one of X and Y is a bond.)

Preferred compounds include a compound (I) of the present invention in which A is an unsaturated lower alkylene group, a group represented by the formula $-(CH_2)_mZ(CH_2)_n-$ or a group represented by the formula $-(CH_2)_mZ(CH_2)_nCR_4=$ and Z is an oxygen atom (—O—), a carbonyl group (—CO—) or a group represented by the formula $-NR_5-$, more preferably a compound (I) of the present invention in which the tricyclic group represented by

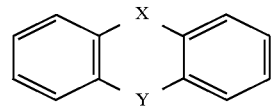

in the general formula (I) is

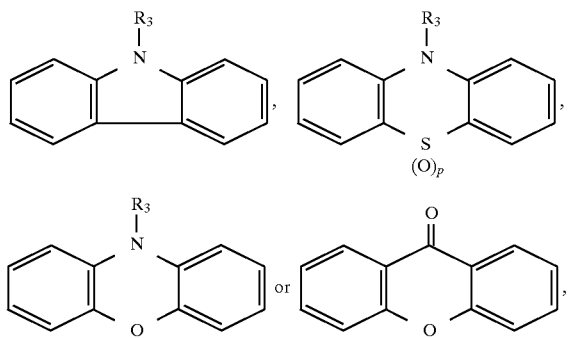

and $R_3$ is a hydrogen atom or a lower alkyl group which may have a hydroxyl group, a lower alkoxy group, an amino group, a mono- or di-lower alkylamino group, a carboxyl group, a lower alkoxycarbonyl group, a carbamoyl group, a mono- or di-lower alkylcarbamoyl group or an aryl group as its substituent, most preferably a compound (I) of the present invention in which A is a group represented by the formula $-(CH_2)_mO(CH_2)_nCR_4=$, and most particularly preferred is (Z)-3-[2-(carbazol-2-yloxy)ethylidene]quinuclidine, a salt thereof, a hydrate thereof or a solvate thereof; (Z)-3-[2-(carbazol-2-yloxy)-1-methylethylidene]quinuclidine, a salt thereof, a hydrate thereof or a solvate thereof; or (E)-3-[2-(carbazol-2-yloxy)-1-fluoroethylidene]quinuclidine, a salt thereof, a hydrate thereof or a solvate thereof.

The pharmaceutical composition as another object of the present invention is a pharmaceutical composition which contains a quinuclidine derivative represented by the general formula (I') or a pharmaceutically acceptable salt thereof as its active ingredient, a pharmaceutical composition which uses the compound (I') of the present invention having squalene synthase inhibiting activity as its active ingredient, a pharmaceutical composition as a cholesterol lowering agent which uses the compound (I') of the present invention having squalene synthase inhibiting activity as its active ingredient, particularly a pharmaceutical composition which uses the compound (I') of the present invention having squalene synthase inhibiting activity as its active ingredient and is a drug for use in the prevention or treatment of hyperlipemia, arteriosclerosis, aneurysm, ischemic heart diseases such as myocardial infarction, angina pectoris and the like and cerebral arteriosclerotic diseases such as cerebral infarction and the like.

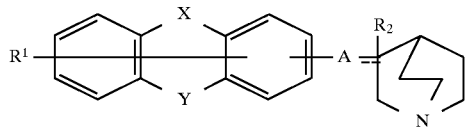

(Symbols in the formula represent the following meanings;

$R_1$: a hydrogen atom, a halogen atom or a lower alkyl group, $R_2$: a hydrogen atom, a hydroxyl group or a lower alkoxy group, $\overline{\cdots}$ : a single bond or a double bond,
   with the proviso that $R_2$ does not exist when $\overline{\cdots}$ is a double bond, X and Y: the same or different from each other and each represents a bond, an oxygen atom (—O—), a carbonyl group (—CO—), a group represented by the formula —S(O)$_p$— or a group represented by the formula —NR$_3$—, p: 0, 1 or 2, $R_3$: a hydrogen atom or a lower alkyl group which may have a substituent, A': a saturated or unsaturated lower alkylene group, a group represented by the formula —(CH$_2$)$_m$Z(CH$_2$)$_n$— or a group represented by the formula —(CH$_2$)$_m$Z(CH$_2$)$_n$CR$_4$=, Z: an oxygen atom (—O—), a group represented by the formula —S(O)$_q$—, a carbonyl group (—CO—) or a group represented by the formula —NR$_5$—, $R_4$: a hydrogen atom, a halogen atom or a lower alkyl group, $R_5$: a hydrogen atom or a lower alkyl group, m and n: the same or different from each other and each is 0 or an integer of 1 to 5, m+n: an integer of 1 to 5, and q: 0, 1 or 2.)

The following describes the compound (I) of the present invention in detail.

In the definition of the formulae of this specification, unless otherwise noted, the term "lower" means a straight or branched carbon chain having 1 to 6 carbon atoms.

Thus, illustrative examples of the "lower alkyl group" include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like, of which alkyl groups having 1 to 4 carbon atoms are preferred, and methyl, ethyl, propyl, isopropyl and butyl groups are particularly preferred.

Illustrative examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like, of which methoxy group and ethoxy group are particularly preferred.

Illustrative examples of the "halogen atom" include fluorine, chlorine, bromine and iodine atoms, of which fluorine and chlorine atoms are preferred and fluorine atom is particularly preferred.

With respect to the "saturated or unsaturated lower alkylene group" of A, the saturated lower alkylene group is a straight or branched alkylene group having 1 to 6 carbon atoms, and its illustrative examples include methylene, ethylene, ethylidene, trimethylene, isopropylidene, propylene, tetramethylene, pentamethylene, hexamethylene and the like, of which alkylene groups having 1 to 4 carbon atoms are preferred.

The unsaturated lower alkylene group means an alkenylene or alkynylene group having 2 to 6 carbon atoms, and its illustrative examples include vinylene (—CH=CH—), propenylene (—CH=CHCH$_2$—), butenylene (—CH=CHCH$_2$CH$_2$—, —CH$_2$CH=CHCH$_2$—), pentenylene (—CH=CHCH$_2$CH$_2$CH$_2$—, —CH$_2$CH=CHCH$_2$CH$_2$—), hexenylene (—CH=CHCH$_2$CH$_2$CH$_2$CH$_2$—, —CH$_2$CH=CHCH$_2$CH$_2$CH$_2$—, —CH$_2$CH$_2$CH=CHCH$_2$CH$_2$—), ethynylene (—C≡C—), propynylene (—C≡CCH$_2$—), butynylene (—C≡CCH$_2$CH$_2$—, —CH$_2$C≡CCH$_2$—), pentynylene (—C≡CCH$_2$CH$_2$CH$_2$—, —CH$_2$C≡CCH$_2$CH$_2$—), hexynylene (—C≡CCH$_2$CH$_2$CH$_2$CH$_2$—, —CH$_2$C≡CCH$_2$CH$_2$CH$_2$—, —CH$_2$CH$_2$C≡CCH$_2$CH$_2$—) and the like, of which ethynylene group is preferred.

Illustrative examples of the group represented by the formula —(CH$_2$)$_m$Z(CH$_2$)$_n$— include —OCH$_2$—, —CH$_2$O—, —COCH$_2$, —CH$_2$CO—, —NHCH$_2$—, —CH$_2$NH—, —N(CH$_3$)CH$_2$—, —CH$_2$N(CH$_3$)—, —N(CH$_2$CH$_3$)CH$_2$—, —CH$_2$N(CH$_2$CH$_3$)—, —NHC(CH$_3$)$_2$(CH$_2$)$_5$—, —CH$_2$OCH$_2$—, —CH$_2$COCH$_2$—, —CH$_2$NHCH$_2$—, —CH$_2$N(CH$_3$)CH$_2$—, —CH$_2$NH(CH$_2$CH$_3$)CH$_2$—, —CH$_2$NHC(CH$_3$)$_2$(CH$_2$)$_5$—, —(CH$_2$)$_2$O—, —(CH$_2$)$_3$O—, —(CH$_2$)$_4$O—, —(CH$_2$)$_5$O— and the like, of which —CH$_2$O—, —CH$_2$NH— and —COCH$_2$ are preferred, and —CH$_2$O— is particularly preferred.

Illustrative examples of the group represented by the formula —(CH$_2$)$_m$Z(CH$_2$)$_n$CR$_4$= include —OCH$_2$CH=, —OCH$_2$C(CH$_3$)=, —OCH$_2$C(CH$_2$CH$_3$)=, —OCH$_2$CF=, —OCH$_2$CCl=, —CH$_2$OCH=, —COCH$_2$CH=, —CH$_2$COCH=, —NHCH$_2$CH=, —CH$_2$NHCH=, —N(CH$_3$)CH$_2$CH=, —CH$_2$N(CH$_3$)CH=, —N(CH$_2$CH$_3$)CH$_2$CH=, —CH$_2$N(CH$_2$CH$_3$)CH=, —CH$_2$OCH$_2$CH=, —CH$_2$COCH$_2$CH=, —CH$_2$NHCH=, —CH$_2$CH(CH$_3$)CH$_2$CH=, —CH$_2$N(CH$_2$CH$_3$)CH$_2$CH=, —CH$_2$NHC(CH$_3$)$_2$CH=, —(CH$_2$)$_2$OCH$_2$CH=, —(CH$_2$)$_3$OCH$_2$CH= and the like, of which —OCH$_2$CH=, —OCH$_2$C(CH$_3$)=, —OCH$_2$CF= and —CH$_2$OCH$_2$CH= are preferred, and —OCH$_2$CF= is particularly preferred.

Examples of the "substituent" of the lower alkyl group which may have a substituent of R$_3$ include a hydroxyl group, a lower alkoxy group, an amino group, a mono- or di-lower alkylamino group, a carboxyl group, a lower alkoxycarbonyl group, a carbamoyl group, a mono- or di-lower alkylcarbamoyl group and an aryl group, and these substituents may be substituted at optional positions.

The following describes the substituents in detail.

The "lower alkoxy group" and "halogen atom" are as defined in the foregoing.

The "aryl group" means a carbocyclic aryl group, and its illustrative examples include phenyl, tolyl, xylyl, biphenyl, naphthyl, anthryl, phenanthryl and the like, of which phenyl is particularly preferred.

The "mono- or di-lower alkylamino group" is a group in which an amino group is substituted with one or two of the aforementioned lower alkyl groups, and its illustrative examples include mono-lower alkylamino groups such as methylamino, ethylamino, propylamino, isopropylamino, butylamino, isobutylamino, sec-butylamino, tert-butylamino, pentyl(amyl)amino, isopentylamino, neopentylamino, tert-pentylamino and the like and di-lower alkylamino groups such as dimethylamino, ethylmethylamino, diethylamino, dipropylamino, diisopropylamino, dibutylamino, diisobutylamino and the like, of which methylamino, ethylamino, dimethylamino and diethylamino groups are preferred, and a dimethylamino group is particularly preferred.

The "lower alkoxycarbonyl group" means a carboxyl group which is substituted with one of the aforementioned lower alkoxy groups, and its illustrative examples include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxy(amyloxy)carbonyl, isopentyloxycarbonyl, tert-pentyloxycarbonyl, neopentyloxycarbonyl, 2-methylbutoxycarbonyl, 1,2-dimethylpropoxycarbonyl, 1-ethylpropoxycarbonyl, hexyloxycarbonyl and the like, of which methoxycarbonyl, ethoxycarbonyl, propoxycarbonyl and isopropoxycarbonyl groups are preferred, and ethoxycarbonyl group is particularly preferred.

The "mono- or di-lower alkylcarbamoyl group" is a carbamoyl group which is substituted with one or two of the aforementioned lower alkyl groups, and its illustrative examples include mono-lower alkylcarbamoyl groups such as methylcarbamoyl, ethylcarbamoyl, propylcarbamoyl, isopropylcarbamoyl, butylcarbamoyl, isobutylcarbamoyl, sec-butylcarbamoyl, tert-butylcarbamoyl, pentyl(amyl)carbamoyl, isopentylcarbamoyl, neopentylcarbamoyl, tert-pentylcarbamoyl and the like and di-lower alkylcarbamoyl groups such as dimethylcarbamoyl, ethylmethylcarbamoyl, diethylcarbamoyl, dipropylcarbamoyl, diisopropylcarbamoyl, dibutylcarbamoyl, diisobutylcarbamoyl and the like, of which methylcarbamoyl, ethylcarbamoyl, dimethylcarbamoyl and diethylcarbamoyl are preferred.

Depending on the type of groups, the compound (I) of the present invention may have an asymmetric carbon atom and a double bond. In consequence, various isomers such as optical isomers, geometrical isomers (cis-form and trans-form) and the like, either in isolated forms or as mixtures, are all included in the compound (I) of the present invention.

The compound (I) of the present invention may form acid addition salts or salts with bases. These salts are also included in the compound of the present invention.

Examples of such salts include acid addition salts with inorganic acids such as hydrochloric acid, hydrobromic acid, hydroiodic acid, sulfuric acid, nitric acid, phosphoric acid and the like, organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid and the like and acidic amino acids such as aspartic acid, glutamic acid and the like, and salts with inorganic bases such as sodium, potassium, magnesium, calcium, aluminum and the like and organic bases such as methylamine, ethylamine, monoethanolamine, diethanolamine, triethanolamine, cyclohexylamine, lysine, ornithine and the like.

Also, the compound (I) of the present invention and salts thereof may be isolated as hydrates, various solvates such as ethanol solvate and the like or polymorphic forms thereof, and these various hydrates, solvates and polymorphic forms are also included in the compound of the present invention.

(Production Method)

The compound of the present invention represented by the general formula (I) can be synthesized, for example, by the following methods, though production methods of the compound of the present invention are not restricted thereby. In addition, since novel intermediates are also included in the present invention, their production methods are also described in detail.

First production method (Synthesis of intermediate)

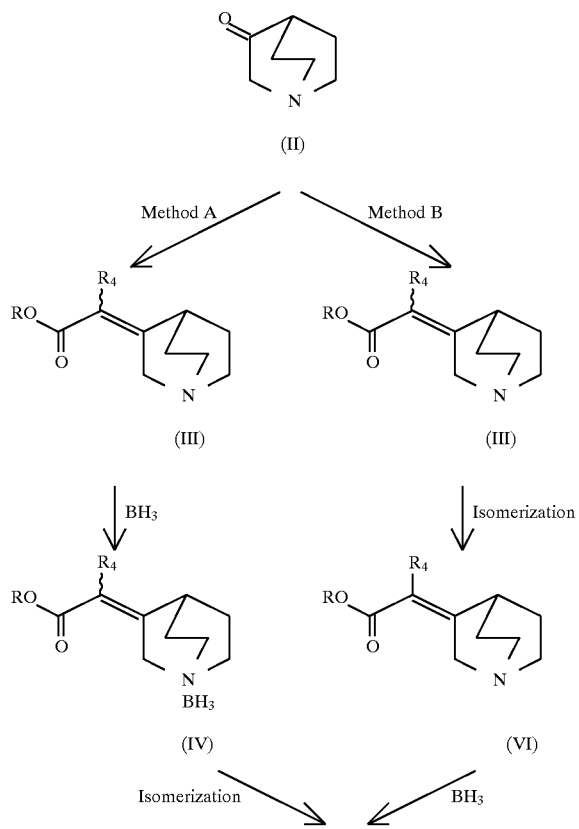

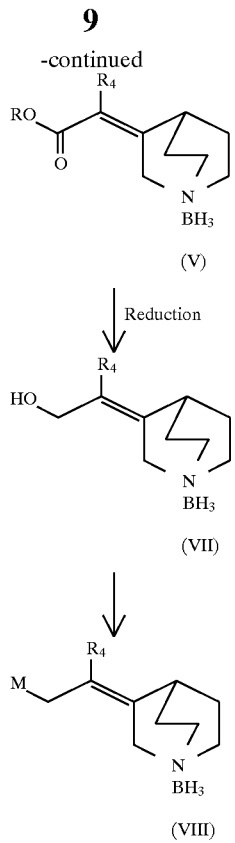

(In the above formulae, R is a lower alkyl group and M is a leaving group.)

As the leaving group, halogen atoms such as chlorine, bromine, iodine and the like and mesyloxy, tosyloxy and the like can be exemplified.

Method A: In this method, 3-quinuclidinone (II) is subjected to the Wittig reaction (first step) to effect formation of a complex with borane (second step) which is isomerized (third step) to give an ester (V), the ester is subjected to a reduction reaction to give an alcohol (VII) (fourth step) and then the hydroxyl group of the alcohol (VII) is converted into a leaving group (fifth step), thereby obtaining a quinuclidine compound (VIII) which is a starting compound for the compound of the present invention. The order of the first step and the second step may be changed.

The Wittig reaction is carried out in the conventional way. Illustratively, the reaction is effected by stirring 3-quinuclidinone (II) and the reaction-corresponding amount, preferably 1 to 2 equivalents, of a Wittig reaction agent (for example, a phosphonic acid derivative such as trimethyl 2-phosphonoacetate, triethyl 2-phosphonoacetate, triisopropyl 2-phosphonoacetate, triethyl 2-fluoro-2-phosphonoacetate (when $R_4$=fluorine atom), triethyl 2-methyl-2-phosphonopropionate (when $R_4$=methyl group) or the like) at room temperature or with heating in an organic solvent inert to the reaction (e.g., methanol, ethanol, isopropanol, tetrahydrofuran (THF), dioxane, diethyl ether, dimethoxyethane, toluene, benzene or the like) in the presence of a base (e.g., sodium alkoxide such as sodium methoxide, sodium ethoxide or the like, metal hydride such as sodium hydride, lithium hydride, potassium hydride or the like, sodium hydroxide, potassium hydroxide, lithium hydroxide, potassium carbonate, sodium bicarbonate, sodium carbonate, or alkyl lithium such as n-butyl lithium or the like). In addition to the just described Wittig reaction agents, various stable ylide compounds such as triph-enylphosphoranylidenacetic acid methyl ester, triphenylphosphoranylidenacetic acid ethyl ester and the like can also be used.

In this production method, 3-quinuclidinone hydrochloride may be used instead of 3-quinuclidinone (II). In that case, it is necessary to add the aforementioned base in an increased amount equivalent to hydrogen chloride.

The borane complex formation reaction is carried out by stirring the quinuclidine compound (III) and the reaction-corresponding amount of borane in the aforementioned organic solvent with ice-cooling.

The isomerization reaction is carried out by stirring the ester (IV) and the reaction-corresponding amount of the aforementioned base in an alcohol such as methanol, ethanol, isopropanol or the like at room temperature or with heating, preferably from room temperature to 50° C.

For example, when R is a methyl group and $R_4$ is a hydrogen atom, the double bond-based geometrical isomer ratio is changed from Z/E=1/1 to 10/1 after isomerization. The geometrical isomers are converted into alcohol by the subsequent reduction reaction (described hereinafter) and then separated easily by silica gel chromatography or the like.

The reduction reaction is carried out by stirring the ester (V) in the presence of the reaction-corresponding amount of a reducing agent (metal hydride such as diisobutylaluminum hydride, lithium aluminum hydride, sodium bis(2-methoxyethoxy)aluminum hydride or the like) in an organic solvent inert to the reaction, such as toluene, THF, diethyl ether, hexane or the like at cooling temperature to room temperature, preferably at −78° C. to 0° C.

The leaving group conversion reaction is carried out by adding methanesulfonyl chloride and lithium chloride to the alcohol (VII) obtained in the above reduction reaction and stirring the mixture in the presence of an amine base (triethylamine or the like) in a solvent inert to the reaction, such as methylene chloride, dimethylformamide (DMF), THF, dioxane, diethyl ether or the like at room temperature.

Method B: In this process, the starting material is subjected to Wittig reaction (first step), isomerized (second step) and then made into a complex with borane (third step), thereby obtaining the ester (V) which is subsequently converted into the quinuclidine compound (VIII) in the same manner as the case of Method A.

Each of these steps is as described in Method A.

Second production method

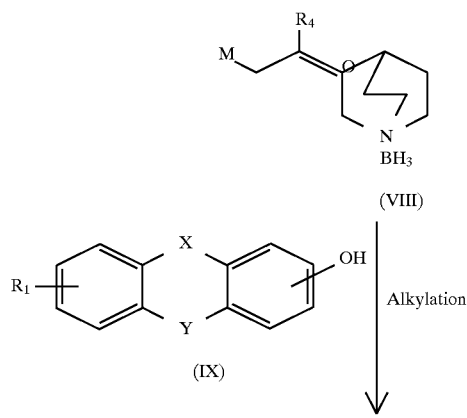

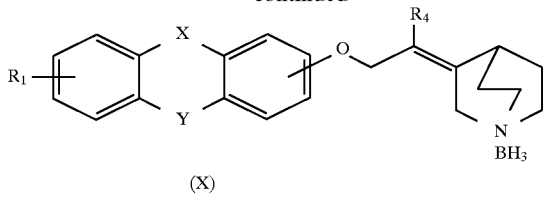

(X)

In this production method, a borane-added form (X) of the compound of the present invention is obtained by subjecting the quinuclidine compound (VIII) and a hydroxy compound (IX) to alkylation reaction. The alkylation reaction is carried out by stirring the quinuclidine compound (VIII) and the reaction-corresponding amount of a hydroxy compound (IX) in the presence of a base (potassium carbonate, sodium carbonate, sodium hydroxide, potassium hydroxide, sodium hydride or alkyl lithium such as n-butyl lithium, or the like) in an organic solvent inert to the reaction, such as dimethylformamide (DMF), dimethyl sulfoxide (DMSO), THF, dioxane, diethyl ether, dimethoxyethane, acetone, acetonitrile or the like at room temperature.

Third production method hydroiodic acid, sulfuric acid, nitric acid or the like, or an organic acid such as a carboxylic acid (e.g., acetic acid, oxalic acid or the like) or an organic sulfonic acid (e.g., methanesulfonic acid, p-toluenesulfonic acid or the like) in an organic solvent inert to the reaction, such as an alcohol (e.g., methanol, ethanol, isopropanol or the like), THF, diethyl ether, DMF or the like. Thereafter, the free-form compound of the present invention (Ia, Ib or Ic) can be obtained by stirring at room temperature in the presence of a base (potassium carbonate aqueous solution, sodium bicarbonate aqueous solution, sodium hydroxide aqueous solution or the like).

Alkylation: This is carried out by stirring the borane complex (X) in which X is NH and the reaction-corresponding amount of an alkylating agent (a halogenoalkyl or the like) in the presence of a base (sodium hydride, potassium hydride, lithium hydride, sodium hydroxide, potassium hydroxide, potassium carbonate or alkyl lithium such as n-butyl lithium, methyl lithium, t-butyl lithium or the like) in an organic solvent inert to the reaction, such as DMF, DMSO, THF, dioxane, diethyl ether, dimethoxyethane, acetonitrile or the like at cooling temperature to room temperature, thereby obtaining the compound (XI) in which $R_3$ is a lower alkyl group which may have an aryl group, a hydroxyl group, a lower alkoxy group, an

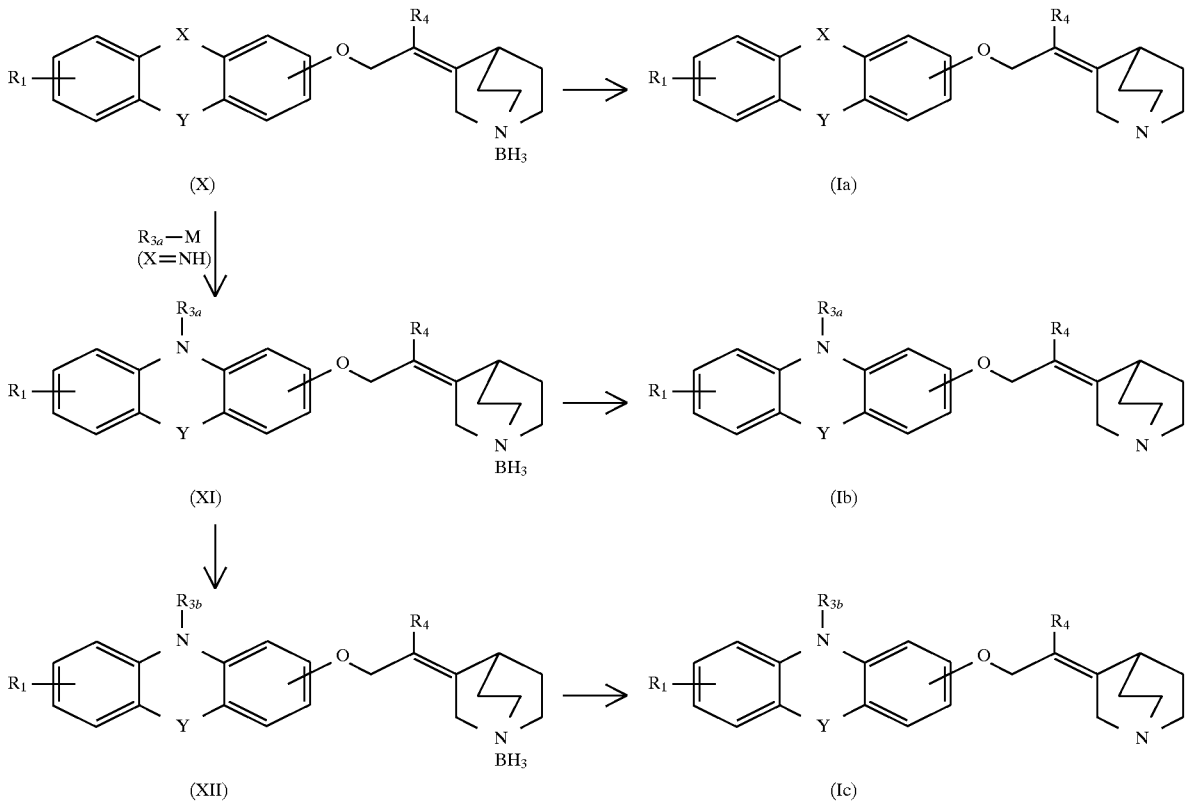

(In the above formulae, $R_{3a}$ and $R_{3b}$ are different from each other and each represents a group of $R_3$ other than a hydrogen atom.)

In this production method, the compound of the present invention is obtained by the elimination of borane, alkylation reaction when X is NH and conversion reaction of the substituent.

Elimination of borane: This is carried out by stirring corresponding borane complex (X, XI or XII) at room temperature or with heating, in the presence of an acid (an inorganic acid such as hydrochloric acid, hydrobromic acid, amino group, a mono- or di-lower alkylamino group, a carboxy group, a lower alkoxycarbonyl group, a carbamoyl group or a mono- or di-lower alkylcarbamoyl group as a substituent.

The substituent conversion reaction, for example, the reaction from an amino-lower alkyl group to a mono- or di-lower alkylamino-lower alkyl group or from a carbamoyl group to a mono- or di-lower alkylcarbamoyl group, can be effected by a method similar to the above alkylation reaction.

Also, the carbazole compound (XI) or (XII) can be synthesized directly from the intermediate (VIII) by the second production method using the compound (IX) in which X is $NR_3$.

Fourth production method

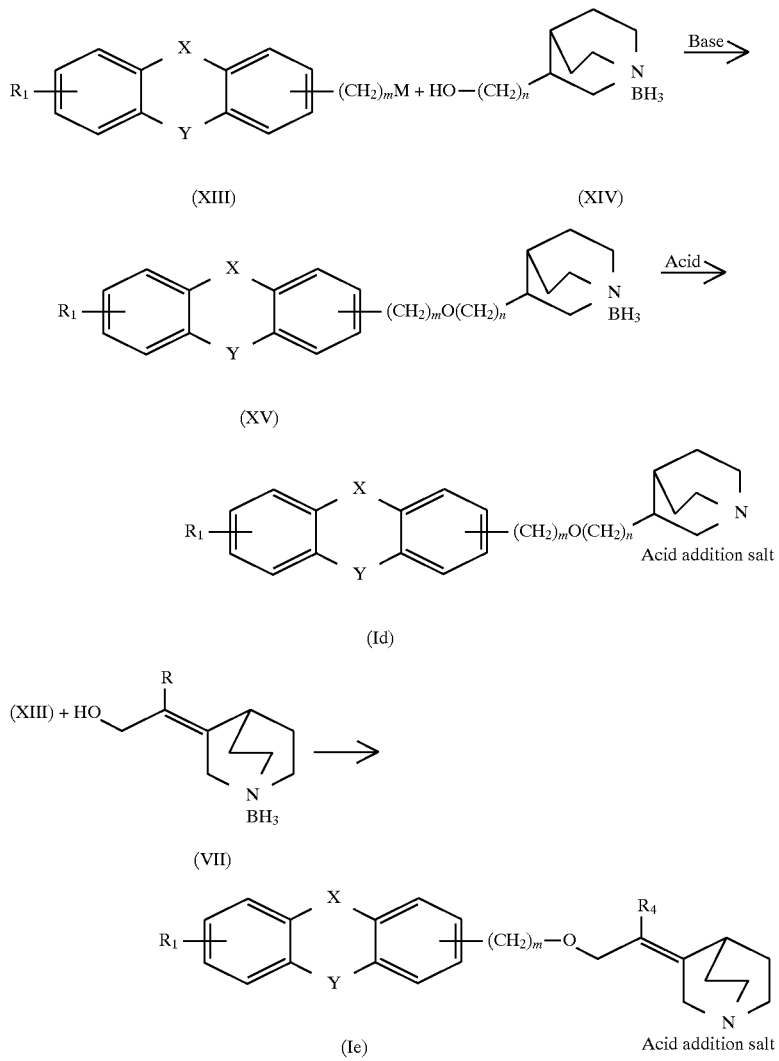

The compound (Id) of the present invention is produced by the elimination of borane (deprotection) from an ether compound (XV) which is obtained by the alkylation of a borane-(3-quinuclidinol) complex (XIV) in the presence of a base.

The alkylation reaction can be effected by the same method of the second production method, and elimination of borane can be effected by the same method of the third production method.

In this production method, a compound of the present invention represented by (Ie) can be produced by carrying out the same reaction using a borane-[3-(2-hydroxyethylidene)quinuclidine] complex (VII) instead of the alcohol (XIV) of the material compound.

Fifth production method

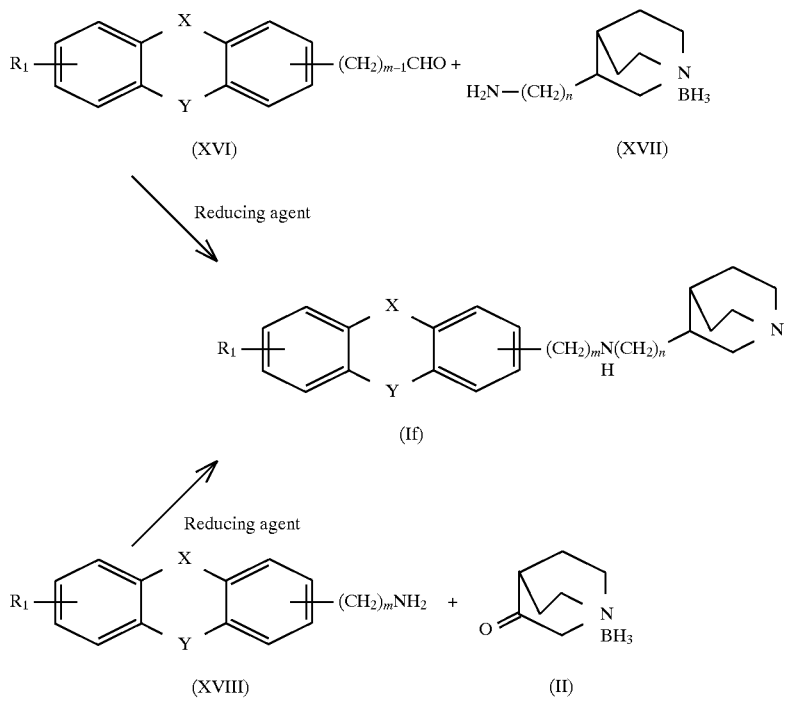

The compound (If) of the present invention is produced by a reductive condensation reaction of an aromatic aldehyde (XVI) with 3-aminoquinuclidine (XVII). This reaction is carried out by using the compound (XVI) and 3-aminoquinuclidine (XVII) in equivalent molar ratio or either one of them in an excess amount, and stirring them at room temperature or with heating, in an organic solvent inert to the reaction; such as dichloromethane, THF, methanol, ethanol, benzene or the like, water, or a mixture solvent thereof, in the presence of a reducing agent, or by subjecting the compound (VI) and the reaction-corresponding amount of 3-aminoquinuclidine (VII) to a condensation reaction without solvent or in a solvent such as benzene, toluene or the like while removing water under azeotropic condition or in the presence of a drying agent, thereby synthesizing a Schiff base, and then carrying out the reduction reaction in a solvent such as ethanol, methanol or the like in the presence of a reducing agent.

Preferred examples of the reducing agent to be used in this reaction include metal hydrides such as sodium borohydride, sodium triacetoxyborohydride, sodium cyanoborohydride and the like. Acid catalysts such as hydrochloric acid, acetic acid and the like may also be used.

When n is 0 in the compound (If) of the present invention, a reductive condensation reaction of the amine compound (XVIII) with 3-quinuclidinone (II) may be used as an alternative method. The reaction conditions, solvents and reducing agents can be set in the same manner as described above.

Sixth production method

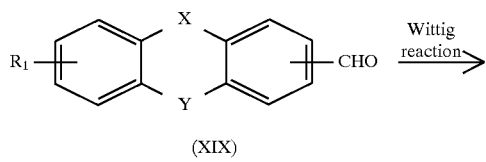

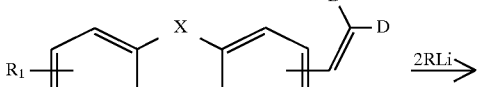

(In the above formulae, R is a lower alkyl group and D is a chlorine atom or a bromine atom.)

The compound (Ig) of the present invention is produced by the following method using an aldehyde (XIX) as the material compound. This production method is effected by allowing a dihalogenoolefin (XX) obtained by the Wittig reaction (first step) to react with 2 equivalents of an organic lithium reagent, and then allowing the resulting lithium acetylide (XXI) to react with 3-quinuclidinone (second step).

Preferably, the Wittig reaction may be carried out by using a Wittig reaction agent prepared by mixing carbon tetrabromide, zinc (dust) and triarylphosphine such as triphenylphosphine or the like in dichloromethane, and allowing the agent to react with the aldehyde (XIX).

Examples of the organic lithium reagent to be used in the second step include n-butyl lithium, methyl lithium, sec-butyl lithium, t-butyl lithium and the like, and examples of the reaction solvent include ethers such as THF, diethyl ether, dimethoxyethane and the like and inert solvents such as cyclohexane, hexane, pentane and the like. Preferably, the compound (Ig) of the present invention can be obtained with high yield by a method in which n-butyl lithium (2 equivalents) is added under cooling (—78° to 0° C.) to THF solution of the compound (XX), and the mixture is warmed to room temperature, cooled again and then allowed to react with 3-quinuclidinone added.

Seventh production method

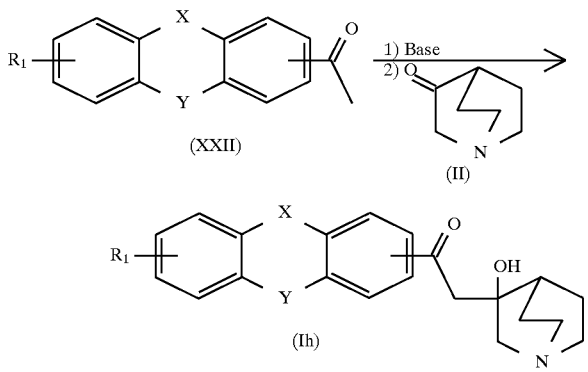

The compound (Ih) of the present invention is produced by allowing a metal enolate, which is formed by the reaction of a methyl aryl ketone (XXII) with a base, to undergo an aldol reaction with 3-quinuclidinone. As the base, metal amides such as lithium diisopropylamide, lithium bis (trimethylsilyl)amide, potassium bis(trimethylsilyl)amide and the like are used preferably. When the compound (XXII) is a phenothiazine derivative which has a lower alkyl substituent at the 10-position, the same mol equivalent of the base is required based on the compound (XXII), while two equivalents of the base is required based on the ketone (XXII) in the case of a phenothiazine derivative which has no substituent at the 10-position. Examples of the reaction solvent include ethers such as THF, diethyl ether, dimethoxyethane and the like which are generally used in the aldol reaction of metal enolate.

As an alternative method, various inorganic metal salts such as zinc chloride, magnesium chloride, titanium tetrachloride and the like are added to the lithium enolate or potassium enolate which is formed when the aforementioned base is used, and then the aldol reaction is carried out by adding 3-quinuclidinone.

The compound (I) of the present invention obtained in this manner is isolated and purified as its free form or as a salt thereof, a hydrate thereof, a solvate thereof or a polymorphic form thereof. Also, salts of the compound (I) of the present invention can be produced by subjecting the compound to usual salt forming reactions.

The isolation and purification are carried out by employing usual chemical operations such as extraction, concentration, distillation, crystallization, filtration, recrystallization, various chromatographic techniques and the like.

Various isomers can be separated by selecting appropriate material compounds or making use of differences in physical properties between isomers. For example, optical isomers can be separated into stereochemically pure isomers by selecting an appropriate material compound or by racemic resolution of racemic compounds (for example, a method in which such compounds are converted into diastereomer salts with general optically active acids or bases and then subjected to optical resolution).

In addition to the compounds described in the Examples, the following compounds can be obtained without requiring special experiments in accordance with the aforementioned production methods, the production methods described in the Examples and their modifications known to those skilled in the art.

3-(10-Propylphenothiazin-3-ylmethoxy)quinuclidine,
3-(10-Isobutylphenothiazin-3-ylmethoxy)quinuclidine,
3-(10-tert-Butylphenothiazin-3-ylmethoxy)quinuclidine,
3-(10-Pentylphenothiazin-3-ylmethoxy)quinuclidine,
3-(10-Hexylphenothiazin-3-ylmethoxy)quinuclidine,
(Z)-3-[2-[9-(3-aminopropyl)carbazol-2-yloxy]ethylidene]quinuclidine,
(E)-3-[2-[9-(3-aminopropyl)carbazol-2-yloxy]ethylidene]quinuclidine,
(Z)-3-[2-[9-(4-aminobutyl)carbazol-2-yloxy]ethylidene]quinuclidine,
(E)-3-[2-[9-(4-aminobutyl)carbazol-2-yloxy]ethylidene]quinuclidine,
(Z)-3-[2-[9-[2-(methylamino)ethyl]carbazol-2-yloxy]ethylidene]quinuclidine,
(E)-3-[2-[9-[2-(methylamino)ethyl]carbazol-2-yloxy]ethylidene]quinuclidine,
(Z)-3-[2-[9-[2-(ethylamino)ethyl]carbazol-2-yloxy]ethylidene]quinuclidine,
(E)-3-[2-[9-[2-(ethylamino)ethyl]carbazol-2-yloxy]ethylidene]quinuclidine,
(Z)-3-[2-[9-[3-(methylamino)propyl]carbazol-2-yloxy]ethylidene]quinuclidine,
(E)-3-[2-[9-[3-(methylamino)propyl]carbazol-2-yloxy]ethylidene]quinuclidine,
(Z)-3-[2-[9-[3-(ethylamino)propyl]carbazol-2-yloxy]ethylidene]quinuclidine,
(E)-3-[2-[9-[3-(ethylamino)propyl]carbazol-2-yloxy]ethylidene]quinuclidine,
(Z)-3-[2-[9-[3-(diethylamino)propyl]carbazol-2-yloxy]ethylidene]quinuclidine.
(E)-3-[2-(carbazol-2-yloxy)-1-chloroethylidene]quinuclidine
(Z)-3-[2-(carbazol-2-yloxy)-1-ethylethylidene]quinuclidine
(Z)-3-[2-(carbazol-2-yloxy)-1-propylethylidene]quinuclidine
(E)-3-[2-(carbazol-2-ylthio)-1-fluoroethylidene]quinuclidine
(Z)-3-[2-(carbazol-2-ylthio)-1-methylethylidene]quinuclidine
(E)-3-[2-(dibenzofuran-3-yloxy)-1-fluoroethylidene]quinuclidine

INDUSTRIAL APPLICABILITY

The compound (I) of the present invention, a pharmaceutically acceptable salt thereof, a hydrate-thereof or a solvate thereof have excellent squalene synthase inhibiting activity and excellent cholesterol biosynthesis inhibiting action in the living body based on this activity. Also, since the compound is effective even in experiments in which human cultured cells are used, it is useful for the prevention or treatment of arteriosclerosis, aneurysm, ischemic heart diseases such as myocardial infarction, angina pectoris and the like and cerebral arteriosclerotic diseases such as cerebral infarction and the like, induced by the action of cholesterol in human and warm-blooded animals, particularly in human.

In addition, since the compound of the present invention selectively inhibits squalene synthase which is an enzyme located at the middle stage of the cholesterol biosynthesis system, it shows extremely lowered side effects or shows no side effects which are common in inhibitors of enzymes located at the early stage or late stage of the cholesterol biosynthesis system, such as inhibition of the synthesis of important metabolic products such as dolichol, ubiquinone, isopentenyl tRNA, p21Ras, low molecular weight G protein and the like and generation of hepatic cytotoxicity (myopathy) caused by the accumulation of toxic substances such as desmosterol.

The squalene synthase inhibiting action and cholesterol biosynthesis inhibiting action of the compound of the present invention have been confirmed by the following methods.

I. Test methods

A. Test on human squalene synthase inhibition (1) Preparation of squalene synthase from human hepatoma cells Human hepatoma cells (HepG2 cells) were cultured using DMEM containing 10% FBS until a single layer was formed, and then the medium was replaced by DMEM supplemented with 10% human lipoprotein deficient serum (LPDS) to carry out 24 hours of culturing. The cells were washed twice with PBS, collected using a Rubber Policeman and subjected to centrifugation. The resulting precipitate was homogenized in five volumes of 50 mM Hepes buffer (pH 7.5) containing 5 mM EDTA and centrifuged at 20,000×g for 15 minutes. The supernatant was again subjected to the same centrifugation. The supernatant was subjected to 1 hour of centrifugation at 100,000×g, and the microsomes obtained were suspended in the same buffer and used in the test as a HepG2 squalene synthase fraction.

(2) Measurement of squalene synthase inhibiting activity

A dimethyl sulfoxide solution of each drug to be tested was added to a solution of the squalene synthase fraction prepared above (protein 10 ng, 50 mM Hepes buffer (pH 7.5)), 11 mM NaF, 5.5 mM $MgCl_2$, 3 mM DTT, 1 mM NADPH, 1 mM pyrophosphate and 2.5 $\mu$M $^3$H-FPP, and the mixture was adjusted to a total volume of 0.2 ml and shaken at 30° C. for 20 minutes to effect the reaction. The reaction was terminated by adding 100 $\mu$l of 20% potassium hydroxide-50% ethanol solution, and the reaction solution was heated at 65° C. for 30 minutes. The un-saponified material was extracted with petroleum ether, and ⅓ volume thereof was subjected to measurement by a liquid scintillation counter. The $^3$H radioactivity of the un-saponified material was regarded as products down stream of squalene in the cholesterol biosynthesis system, and the squalene synthase inhibiting action was calculated by comparing $^3$H radioactivities of the test group and control group.

In addition, concentration of each compound of the present invention to inhibit 50% of squalene synthase ($IC_{50}$ value) was obtained by calculation.

B. Inhibition test of rat squalene synthase (1) Preparation of rat squalene synthase An male SD rat loaded with 3% colestyramine feed for 2 weeks was sacrificed by bleeding to excise the liver which was subsequently homogenized in five volumes of 50 mM Hepes buffer (pH 7.5) containing 5 mM EDTA and centrifuged at 20,000×g for 15 minutes. The supernatant was again subjected to the same centrifugation. The supernatant was further subjected to 1 hour of centrifugation at 100, 000×g, and the resulting microsomes were suspended in the same buffer and used in the test as a squalene synthase fraction.

(2) Squalene synthase inhibiting activity was measured by the same method of the above item A (2).

C. Cholesterol lowering action in hamster

Male golden hamsters (130 to 150 g) which have been treated by reversing night and day since 12 or more days before the commencement of administration were divided into groups 4 days before the administration in such a manner that the cholesterol value became the same among the groups. Each drug was prepared as a 0.5% methyl cellulose solution and administered by force in a dosage of 50 mg/kg. In this case, the liquid volume was 10 ml/kg.

The administration was carried out continuously for 4 days at around A.M. 11:00 under satiated condition and then on the fifth day after 16 hours of fasting. After 2 hours of the final administration, blood samples were collected from the abdominal vena cava under diethyl ether anesthesia and their cholesterol values were measured using an automatic analyzer (Hitachi 736).

II. Test results

The measured results of each compound of the present invention are shown in the following.

(1) Results of the inhibition test on squalene synthase derived from human hepatoma cell The $IC_{50}$ value of squalene synthase inhibiting activity was calculated by the aforementioned test method (A), with the results shown in Table 1.

TABLE 1

| Compound | $IC_{50}$ value |
|---|---|
| Example 1 | 79 nM |
| Example 2 | 59 nM |
| Example 17 | 85 nM |

As the result, each compound of the present invention showed strong activity to inhibit squalene synthase prepared from human hepatoma cells.

In addition, the compounds of the present invention showed clear inhibiting action also in the rat squalene synthase inhibition test within the concentration range of approximately from 0.01 to 25 $\mu$M.

(2) Cholesterol lowering action in hamster

The cholesterol lowering action was measured by the aforementioned test method (C), with the results on the lowering ratio shown in Table 2.

TABLE 2

| Compound | Lowering ratio (%) |
|---|---|
| Example 1 | 57 |
| Example 2 | 39 |
| Example 17 | 46 |

As the result, the compounds of the present invention showed strong action to lower cholesterol level.

Thus, the compounds of the present invention showed strong activity to inhibit human squalene synthase and strong action to lower cholesterol level in hamster. In consequence, the compounds of the present invention are useful for the treatment or prevention of various diseases induced by the action of cholesterol (arteriosclerosis, aneurysm, ischemic heart diseases such as myocardial infarction, angina pectoris and the like and cerebral arteriosclerotic diseases such as cerebral infarction and the like).

The pharmaceutical composition which contains one or two or more of the compound (I) of the present invention, pharmaceutically acceptable salts thereof, hydrates thereof and solvates thereof as the active ingredient is prepared into tablets, powders, fine powders, granules, capsules, pills, solutions, injections, suppositories, ointments, adhesive preparations and the like using generally used pharmaceutical carriers, excipients and other additives and administered orally (including sublingual administration) or parenterally.

Clinical dose of the compound (I) of the present invention in human is appropriately decided by taking symptoms, age, sex and the like of each patient to be treated into consideration, but the compound may be administered orally generally within the range of from 10 mg to 500 mg, preferably from 100 mg to 500 mg, per day per adult, by dividing the daily dose into one to several doses per day, or within the range of from 1 mg to 100 mg, preferably from 10 mg to 100 mg, per day per adult, by intravenous administration by dividing the daily dose into one to several doses per day, or by continuous intravenous administration within the range of from 1 hour to 24 hours per day. As a matter of course, since the dosage varies under various conditions, a smaller dosage than the above range may be sufficient enough in some cases.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium metasilicate. In the conventional way, the composition may contain additives other than the inert diluent, such as lubricants (e.g., magnesium stearate or the like), disintegrating agents (e.g., calcium cellulose glycolate or the like), stabilizing agents (e.g., lactose or the like), and solubilization assisting agent (e.g., glutamic acid, aspartic acid or the like). If necessary, tablets or pills may be coated with a film of a gastric soluble or enteric soluble substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol. In addition to the inert diluent, this composition may also contain auxiliary agents such as a solubilizing or solubilization assisting agent, a moistening agent, a suspending agent and the like, as well as sweeteners, flavors, aromas and antiseptics.

The injections for parenteral administration includes aseptic aqueous or non-aqueous solutions, suspensions and emulsions. Examples of the aqueous solutions and suspensions include distilled water for injection use and physiological saline. Examples of the non-aqueous solutions and suspensions include propylene glycol, polyethylene glycol, plant oils (e.g., olive oil or the like), alcohols (e.g., ethyl alcohol or the like), polysorbate 80 (trade name) and the like. Such a composition may further contain additive agents such as a tonicity agent, an antiseptic, a moistening agent, an emulsifying agent, a dispersing agent, a stabilizing agent (e.g., lactose) and a solubilizing or solubilization assisting agent. These compositions are sterilized by filtration through a bacteria retaining filter, blending of a germicide or irradiation. Alternatively, they may be used by firstly making into sterile solid compositions and dissolving them in sterile water or a sterile solvent for injection use prior to their use.

BEST MODE OF CARRYING OUT THE INVENTION

The following illustratively describes the present invention with reference to Examples though the present invention is not restricted thereby. In this connection, novel material compounds to be used in the Examples are also described as Reference Examples.

Reference Example 1

Borane-[ethyl fluoro-(3-quinuclidinylidene)acetate] complex

Sodium hydride (60 wt. %, 83.6 g, 2.09 mol) was added to a mixture of triethyl 2-fluoro-2-phosphonoacetate (506 g, 2.09 mol) and THF (3.0 l) with ice-cooling, and the mixture was stirred for 2 hours. A THF (600 ml) solution of 3-quinuclidinone (238 g, 1.90 mol) was added and the mixture was stirred at room temperature for 5 days. Water (500 ml) was added to the reaction mixture and the mixture was concentrated under a reduced pressure. Water (2.5 l) was added to the residue, and then the reaction product was extracted with chloroform (1.5 l×2). The extract was washed with saturated sodium chloride aqueous solution, dried over anhydrous magnesium sulfate and then concentrated under a reduced pressure. THF (1.0 l) was added to the resulting yellow oily material, and then a borane-THF complex (1.0M THF solution, 2.1 l, 2.1 mol) was added dropwise with ice-cooling spending 2.5 hours. After additional 0.5 hour of stirring, water (400 ml) was added to the reaction mixture and the mixture was concentrated under a reduced pressure. Ethyl acetate was added to the resulting residue, the mixture was washed with water and saturated sodium chloride aqueous solution in that order, dried over anhydrous magnesium sulfate, and then concentrated under a reduced pressure. The resulting residue was washed with hexane (400 ml) and dried under a reduced pressure. Ethanol (2.8 l) was added to the resulting brown solid (402 g) and then, while heating at 50° C., sodium hydride (60 wt. %, 4.24 g, 106 mmol) was added, and the mixture was stirred for 7 hours. After spontaneous cooling, acetic acid (5.4 ml) was added to the reaction mixture, and the mixture was concentrated under a reduced pressure. Ethyl acetate was added to the residue, and the mixture was washed with water and saturated sodium chloride aqueous solution in that order, dried over anhydrous magnesium sulfate, and then concentrated under a reduced pressure. Ethanol (1.2 l) was added to the resulting brown solid, and the mixture was stirred for 20 minutes. The insoluble matter was removed by filtration and then the resulting filtrate was concentrated under a reduced pressure to give the title compound (304 g, E/Z mixture) as a brown oil.

Mass spectrometry data (m/z): 213 ($M^+$)

Reference Example 2

Borane-[(E)-3-(1-fluoro-2-hydroxyethylidene)quinuclidine] complex

A mixture of sodium bis(2-methoxyethoxy)aluminum hydride (70 wt. % toluene solution, 425 g, 1.47 mol) and toluene (800 ml) was added dropwise (2.5 hours) to a mixture of borane-[ethyl fluoro-(3-quinuclidinylidene) acetate] complex (304 g, E/Z mixture) and toluene (800 ml) while keeping the inner temperature at −45° to −35° C., and the mixture was stirred for additional 1 hour. A 2N sodium hydroxide aqueous solution (1.5 l) was added to the reaction mixture, and the mixture was stirred at room temperature for 1 hour. The insoluble matter was removed by filtration and the reaction product was extracted with ethyl acetate. The extract was washed with saturated sodium chloride aqueous solution, dried over anhydrous magnesium sulfate, and then concentrated under a reduced pressure. The resulting residue was purified by silica gel column chromatography (eluent; ethyl acetate:hexane =25:75 then 35:65) to give the title compound (115 g, 0.62 mol, 46%) as colorless crystals.

Nuclear magnetic resonance spectrum ($CDCl_1$, TMS internal standard)

δ: 1.30–1.80 (3H, br), 1.80–1.90 (4H, m), 1.99 (1H, m), 3.00–3.15 (4H, m), 3.67 (2H, s), 4.13 (2H, m).

Reference Example 3

Borane-[(E)-3-(2-chloro-1-fluoroethylidene)quinuclidine] complex

Lithium chloride (55.1 g, 1.3 mol) and methanesulfonyl chloride (40 ml, 520 mmol) were added in that order to a solution of borane-[(E)-3-(1-fluoro-2-hydroxyethylidene) quinuclidine] complex (80.1 g, 433 mmol), dichloromethane (650 ml) and triethylamine (120 ml, 866 mmol) with ice-cooling, the mixture was stirred for 1 hour and then at room temperature for 5 hours. The reaction mixture was concentrated under a reduced pressure, water was added to the residue, and the reaction product was extracted with ethyl acetate. The extract was washed with saturated sodium chloride aqueous solution, dried over anhydrous magnesium sulfate, and then concentrated under a reduced pressure to give the title compound (75.5 g, 371 mmol, 86%) as colorless crystals.

Nuclear magnetic resonance spectrum ($CDCl_3$, TMS internal standard)

δ: 1.30–1.80 (3H, m), 1.80–1.95 (5H, m), 3.00–3.15 (4H, m), 3.64 (2H, s), 4.03 (2H, d).

Reference Example 4

Borane-[(E)-3-[2-(carbazol-2-yloxy)-1-fluoroethylidene] quinuclidine] complex

Potassium carbonate (97 g, 700 mmol) was added to a mixture of borane-[(E)-3-(2-chloro-1-fluoroethylidene) quinuclidine] complex (75.3 g, 370 mmol), 2-hydroxycarbazole (64.5 g, 352 mmol) and DMF (400 ml), and the mixture was stirred at room temperature for 8.5 hours. The reaction mixture was poured into water (2.0 l) and the mixture was stirred for 1 hour. The insoluble matter was collected by filtration, washed with water, methanol and diethyl ether, and then dried under a reduced pressure. By recrystallizing the resulting crystals from ethyl acetate, the title compound (107.0 g, 306 mmol, 87%) was obtained.

Nuclear magnetic resonance spectrum (DMSO-$d_6$, TMS internal standard)

δ: 1.09 (3H, brs), 1.55–1.92 (4H, m), 2.47–2.55 (1H, m), 2.85–3.05 (4H, m), 3.64 (2H, d, J=3 Hz), 4.72 (2H, d, J=21 Hz); 6.84 (1H, dd, J=1 Hz, 9 Hz), 7.03–7.50 (4H, m), 7.95 (1H, s), 8.04 (1H, s).

The compounds of Reference Examples 5 and 6 were obtained in the same manner as in Reference Examples 1 to 4.

Reference Example 5

Borane-[(Z)-3-[2-(carbazol-2-yloxy)ethylidene] quinuclidine] complex

Material compounds: 3-quinuclidinone, trimethyl 2-phosphonoacetate, 2-hydroxycarbazole Nuclear magnetic resonance spectrum ($CDCl_3$, TMS internal standard)

δ: 1.80–1.88 (2H, m), 1.93–2.02 (2H, m), 2.70–2.74 (1H, m), 3.22–3.32 (4H, m), 4.14 (2H, s), 4.60 (2H, d, J=7 Hz), 5.74–5.76 (1H, m), 6.76–6.80 (1H, m), 6.98–7.00 (1H, m), 7.10–7.14 (1H, m), 7.28–7.32 (1H, m), 7.62 (1H, d, J=8 Hz), 7.94–8.00 (2H, m).

Reference Example 6

Borane-[(Z)-3-[2-(carbazol-2-yloxy)-1-methylethylidene] quinuclidine] complex

Material compounds: 3-quinuclidinone, trimethyl 2-phosphonopropionate, 2-hydroxycarbazole Nuclear magnetic resonance spectrum ($CDCl_3$, TMS internal standard)

δ: 1.09 (3H, brs), 1.49 (3H, s), 1.65–1.87 (4H, m), 2.78–3.19 (5H, m), 3.73 (2H, s), 3.99 (2H, s), 6.67–6.83 (1H, m), 7.09–7:43 (4H, m), 7.68–8.05 (2H, m), 8.73 (1H, brs).

Reference Example 7

Borane-[ethyl (Z)-[2-[2-(3-quinuclidinylidene)ethoxy] carbazol-9-yl]acetate] complex In an atmosphere of argon, sodium hydride (60 wt. %, 0.78 g, 19.6 mmol) was added at 0° C. to a mixture of borane-[(Z)-3-[2-(9-carbazol-2-yloxy)ethylidene] quinuclidine] complex (5.93 g, 17.8 mmol) and DMF (35 ml), and the mixture was stirred for 30 minutes. Ethyl bromoacetate (2.38 ml, 21.4 mmol) was added and the mixture was stirred for 1 hour. The reaction mixture was concentrated under a reduced pressure, ethyl acetate and saturated sodium chloride aqueous solution (60 ml for each) were added to the resulting residue in that order, and the reaction product was extracted with ethyl acetate. The extract was dried over anhydrous magnesium sulfate and concentrated under a reduced pressure to give the title compound (7.40 g, 17.7 mmol, 99%) as brown oil.

Nuclear magnetic resonance spectrum ($CDCl_3$, TMS internal standard)

δ: 0.94 (3H, brs), 1.24 (3H, t, J=7 Hz), 1.76–1.98 (4H, m), 1.51–1.65 (1H, m), 2.86–3.19 (4H, m), 3.78 (2H, s), 4.21 (2H, q, J=7 Hz), 4.54 (2H, d, J=6 Hz), 4.93 (2H, s), 5.57–5.78 (1H, m), 6.79–6.88 (2H, m), 7.21–7.34 (3H, m), 7.90–8.04 (2H, m).

Reference Example 8

Borane-[(Z)-3-[2-[9-(2-hydroxyethyl)carbazol-2-yloxy] ethylidene]quinuclidine] complex In an atmosphere of argon, diisobutyl aluminum hydride (0.93M, 56.5 ml toluene solution, 52.5 mmol) was added at −78° C. to a mixture of borane-[ethyl (Z)-[2-[2-(3-quinuclidinylidene)ethoxy]carbazol-9-yl]acetate] complex (7.33 g, 17.5 mmol) and toluene (86 ml), and the mixture was stirred for 2 hours. Methanol (4.4 ml) and water (7.4 ml) were added in that order and the mixture was stirred for 1 hour at room temperature. The insoluble matter was removed by filtration and the resulting filtrate was concentrated under a reduced pressure to give the title compound (5.92 g, 15.7 mmol, 90%) as colorless crystals.

Nuclear magnetic resonance spectrum ($CDCl_3$, TMS internal standard)

δ: 1.24 (3H, brs), 1.76–1.98 (4H, m), 2.56–2.66 (1H, m), 2.97–3.15 (4H, m), 3.77 (2H, s), 4.04 (2H, t, J=5 Hz), 4.36–4.58 (4H, m), 5.57–5.78 (1H, m), 6.77–6.95 (2H, m), 7.12–7.43 (3H, m), 7.90–8.03 (2H, m).

Reference Example 9

Borane-[(Z)-3-[2-[9-(2-aminoethyl)carbazol-2-yloxy] ethylidene]quinuclidine] complex A mixture of borane-[(Z)-3-[2-[9-(2-hydroxyethyl) carbazol-2-yloxy]ethylidene]quinuclidine] complex (3.60 g, 9.57 mmol), THF (19 ml), phthalimide (1.83 g, 19.8 mmol), triphenylphosphine (3.26 g, 19.8 mmol) and diethyl azodicarboxylate (1.92 ml, 19.8 mmol) was stirred at room temperature for 14 hours. The reaction mixture was concentrated under a reduced pressure, and the resulting residue was purified by silica gel column chromatography (eluent; chloroform:methanol=100:1). To a mixture thereof with ethanol (80 ml) was added hydrazine monohydrate (2 ml) at room temperature, and the resulting mixture was heated under reflux for 8 hours. The precipitate was removed by filtration, and the filtrate was concentrated under a reduced pressure. The resulting residue was purified by silica gel column chromatography (eluent; chloroform:methanol:17% aqueous ammonia=100:3:0.3) to give the title compound (1.52 g, 4.05 mmol, 42.3%) as colorless crystals.

Nuclear magnetic resonance spectrum ($CDCl_3$, TMS internal standard)

δ: 1.48 (3H, brs), 1.79–2.01 (4H, m), 2.55–2.69 (1H, m), 2.88–3.19 (6H, m), 3.81 (2H, s), 4.35 (2H, t, J=6 Hz), 4.57 (2H, d, J=6 Hz), 6.61–6.76 (1H, m), 6.80–6.94 (2H, m), 7.29–7.80 (3H, m), 7.92–8.04 (2H, m).

Reference Example 10

Borane-[(Z)-3-[2-[9-(2-methoxyethyl)carbazol-2-yloxy]ethylidene]quinuclidine] complex In an atmosphere of argon, sodium hydride (60 wt. %, 0.19 g, 4.79 mmol) was added at 0° C. to a mixture of borane-[(Z)-3-[2-[9-(2-hydroxyethyl)carbazol-2-yloxy]ethylidene]quinuclidine] complex (1.20 g, 3.19 mmol) and DMF (16 ml), and the mixture was stirred for 30 minutes. Methyl iodide (0.30 ml, 4.79 mmol) was added and the mixture was stirred for 1 hour. The reaction mixture was concentrated under a reduced pressure, ethyl acetate and saturated sodium chloride aqueous solution (each 30 ml) were added to the resulting residue in that order, and then the reaction product was extracted with ethyl acetate. The extract was dried over anhydrous magnesium sulfate and concentrated under a reduced pressure to give the title compound (1.24 g, 3.18 mmol, 100%) as colorless crystals.

Nuclear magnetic resonance spectrum ($CDCl_3$, TMS internal standard)

δ: 0.91 (3H, brs), 1.78–2.00 (4H, m), 2.52–2.63 (1H, m), 2.99–3.15 (4H, m), 3.30 (3H, s), 3.70 (4H, m), 4.19 (2H, t, J=5 Hz), 4.56 (2H, d, J=6 Hz), 5.60–5.79 (1H, m), 5.60–5.79 (1H, m), 5.76–5.95 (2H, m), 7.15–7.41 (3H, m), 7.89–8.05 (2H, m).

Reference Example 11

10-Ethyl-3-formylphenothiazine

N-Methylformanilide (5.35 ml, 43.6 mmol) and phosphorus oxychloride (4.06 ml, 43.6 mmol) were added at room temperature to a mixture of 10-ethylphenothiazine (7.62 g, 33.5 mmol) and 1,2-dichlorobenzene (34 ml), and the mixture was stirred at 100° C. for 24 hours. At room temperature, a sodium acetate aqueous solution (45 wt. %, 85 g) was added to the reaction mixture, which was subsequently concentrated under a reduced pressure. Ethyl acetate and water (each 300 ml) were added to the resulting residue in that order and then the reaction product was extracted with ethyl acetate. The extract was dried over anhydrous magnesium sulfate and then concentrated under a reduced pressure. The resulting residue was purified by silica gel column chromatography (eluent; hexane:ethyl acetate=5:1) to give the title compound (5.91 g, 23.1 mmol, 69%) as yellow crystals.

Nuclear magnetic resonance spectrum ($CDCl_3$, TMS internal standard)

δ: 1.44 (3H, t, J=7 Hz), 3.96 (2H, q, J=7 Hz), 6.84–7.25 (5H, m), 7.56–7.68 (2H, m), 9.78 (1H, s).

The compounds of Reference Examples 12 and 13 were obtained in the same manner as in Reference Example 11.

Reference Example 12

10-Butyl-3-formylphenothiazine

Material compound: 10-butylphenothiazine

Nuclear magnetic resonance spectrum ($CDCl_3$, TMS internal standard)

δ: 0.95 (3H, t, J=7 Hz), 1.26–1.89 (4H, m), 3.89 (2H, t, J=7 Hz), 6.84–7.60 (7H, m), 9.78 (1H, s).

Reference Example 13

3-Formyl-10-(1-methylethyl)phenothiazine

Material compound: 10-(1-methylethyl)phenothiazine

Nuclear magnetic resonance spectrum ($CDCl_3$, TMS internal standard)

δ: 1.68 (6H, d, J=7 Hz), 4.22–4.54 (1H, m), 6.57–7.66 (7H, m), 9.79 (1H, s).

Reference Example 14

3-Hydroxymethyl-10-methylphenothiazine

With ice-cooling, sodium borohydride (4.16 g, 110 mmol) was added to a mixture of 3-formyl-10-methylphenothiazine (24.6 g, 102 mmol), THF (100 ml) and ethanol (100 ml), the mixture was stirred for 10 minutes and then at room temperature for 20 minutes. The solvent was evaporated under a reduced pressure, water and 2N hydrochloric acid were added to the residue in that order, and then the reaction product was extracted with ethyl acetate. The extract was washed with a saturated sodium bicarbonate aqueous solution and saturated sodium chloride aqueous solution in that order, dried over anhydrous magnesium sulfate, and then concentrated under a reduced pressure. By recrystallizing the resulting residue from ethyl acetate-hexane, the title compound (18.9 g, 77.7 mmol, 76%) was obtained as yellow crystals.

Nuclear magnetic resonance spectrum ($CDCl_3$, TMS internal standard)

δ: 3.37 (3H, s), 4.57 (2H, d, J=6 Hz), 6.73–7.52 (7H, m).

The compounds of Reference Examples 15 to 18 were obtained in the same manner as in Reference Example 14.

Reference Example 15

10-Ethyl-3-hydroxymethylphenothiazine

Material compound: 10-ethyl-3-formylphenothiazine

Nuclear magnetic resonance spectrum ($CDCl_3$, TMS internal standard)

δ: 3.37 (3H, m), 4.57 (2H, d, J=6 Hz), 6.73–7.52 (7H, m).

Reference Example 16

10-Butyl-3-hydroxymethylphenothiazine

Material compound: 10-butyl-3-formylphenothiazine

Nuclear magnetic resonance spectrum ($CDCl_3$, TMS internal standard)

δ: 0.97 (3H, t, J=7 Hz), 1.20–1.87 (4H, m), 3.84 (2H, t, J=7 Hz), 4.56 (2H, s), 6.57–7.34 (7H, m).

Reference Example 17

3-Hydroxymethyl-10-(1-methylethyl)phenothiazine

Material compound: 3-formyl-10-(1-methylethyl)phenothiazine

Nuclear magnetic resonance spectrum ($CDCl_3$, TMS internal standard)

δ: 1.61 (6H, d, J=7 Hz), 4.12–4.43 (1H, m), 4.56 (2H, s), 6.57–7.25 (7H, m).

Reference Example 18
3-Hydroxymethyl-10-methylphenoxazine
Material compound: 3-formyl-10-methylphenoxazine
Nuclear magnetic resonance spectrum (CDCl$_3$, TMS internal standard)
δ: 3.04 (3H, s), 4.52 (2H, s), 6.43–6.95 (7H, m).

Reference Example 19
3-Hydroxymethyl-10-methylphenothiazine-5-oxide
With ice-cooling, m-chloroperbenzoic acid (1.66 g, 9.6 mmol) was added to a mixture of 3-hydroxymethyl-10-methylphenothiazine (1.94 g, 8.0 mmol) and dichloromethane (30 ml), and the mixture was stirred for 1.5 hours and then at room temperature for 1.5 hours. A saturated sodium bicarbonate aqueous solution was added to the reaction mixture and the reaction product was extracted with chloroform. The extract was dried over anhydrous magnesium sulfate and then concentrated under a reduced pressure. The resulting residue was purified by silica gel column chromatography (eluent; methanol:chloroform=3:97 then 10:90) to give the title compound (1.95 g, 7.52 mmol, 94%) as colorless crystals.
Nuclear magnetic resonance spectrum (CDCl$_3$, TMS internal standard)
δ: 2.33 (1H, t), 3.76 (3H, s), 4.79 (2H, d), 7.25 (1H, m), 7.35–7.90 (2H, m), 7.60–7.65 (2H, m), 7.89 (1H, d), 7.92 (1H, m).

Reference Example 20
3-Hydroxymethyl-10-methylphenothiazine-5,5-dioxide
With ice-cooling, m-chloroperbenzoic acid (2.59 g, 15 mmol) was added to a mixture of 3-hydroxymethyl-10-methylphenothiazine (1.22 g, 5.0 mmol) and dichloromethane (15 ml), and the mixture was stirred at 0° C. for 30 minutes and then at room temperature for 18 hours. The reaction mixture was diluted with ethyl acetate, washed with a saturated sodium bicarbonate aqueous solution and saturated sodium chloride aqueous solution in that order, dried over anhydrous magnesium sulfate, and then concentrated under a reduced pressure. The resulting residue was purified by silica gel column chromatography (eluent; ethyl acetate:hexane=1:3 then 1:0) to give the title compound (1.23 g, 4.47 mmol, 89%) as yellow crystals.
Nuclear magnetic resonance spectrum (CDCl$_3$, TMS internal standard)
δ: 3.70 (3H, s), 4.75 (2H, s), 7.25–7.30 (3H, m), 7.60–7.65 (2H, m), 8.05–8.10 (2H, m).

Reference Example 21
3-Chloromethyl-10-methylphenothiazine
With ice-cooling, methanesulfonyl chloride (3.9 ml, 50 mmol) was added dropwise to a mixture of 3-hydroxy-10-methylphenothiazine (10.9 g, 45 mmol), triethylamine (8.2 ml, 59 mmol) and dichloromethane (80 ml), and the mixture was stirred at room temperature for 1 hour. Water was added to the reaction mixture and the reaction product was extracted with chloroform. The extract was washed with a saturated sodium bicarbonate aqueous solution and saturated sodium chloride aqueous solution in that order, dried over anhydrous magnesium sulfate, and concentrated under a reduced pressure to give the title compound (8.09 g, 30.9 mmol, 69%) as yellow crystals.
Nuclear magnetic resonance spectrum (CDCl$_3$, TMS internal standard)
δ: 3.36 (3H, s), 4.47 (2H, s), 6.71 (1H, d), 6.77 (1H, d), 6.93 (1H, m), 7.10–7.20 (4H, m).
The compound of Reference Example 22 was obtained in the same manner as in Reference Example 21.

Reference Example 22
3-Chloromethyl-10-methylphenothiazine-5-oxide
Material compounds: 3-hydroxymethyl-10-methylphenothiazine-5-oxide and methanesulfonyl chloride
Nuclear magnetic resonance spectrum (CDCl$_3$, TMS internal standard)
δ: 3.77 (3H, s), 4.65–4.70 (2H, m), 7.28 (1H, m), 7.35–7.40 (2H, m), 7.60–7.65 (2H, m), 7.90–7.95 (2H, m).

Reference Example 23
3-Chloromethyl-10-methylphenothiazine-5,5-dioxide
Thionyl chloride (5 ml) was added to a mixture of 3-hydroxymethyl-10-methylphenothiazine-5,5-dioxide (1.23 g, 4.47 mmol) and chloroform (15 ml), and the mixture was stirred for 1 hour. The reaction mixture was concentrated under a reduced pressure, water was added to the residue, and the reaction product was extracted with chloroform. The extract was washed with water and saturated sodium chloride aqueous solution in that order, dried over anhydrous magnesium sulfate, and then concentrated under a reduced pressure to give the title compound (1.32 g, 100%) as colorless crystals.
Nuclear magnetic resonance spectrum (CDCl$_3$, TMS internal standard)
δ: 3.71 (3H, s), 4.64 (2H, s), 7.25–7.30 (3H, m), 7.60–7.65 (2H, m), 8.05–8.10 (2H, m).

Reference Example 24
3-(2,2-Dibromovinyl)-10-methylphenothiazine
In an atmosphere of argon, carbon tetrabromide (8.29 g, 25 mmol) and zinc powder (1.63 g, 25 mmol) were added in that order to a mixture of triphenylphosphine (6.56 g, 25 mmol) and dichloromethane (75 ml), and the mixture was stirred at room temperature for 23 hours. A dichloromethane (25 ml) solution of 3-formyl-10-methylphenothiazine (3.02 g, 12.5 mmol) was added and the mixture was again stirred for 7 hours. The reaction mixture was diluted with hexane and the insoluble matter was removed by filtration. The reaction product was extracted from the insoluble matter three times with hexane (about 60° C.), and the thus collected organic layers were combined and concentrated under a reduced pressure. The resulting residue was purified by silica gel column chromatography (eluent; ethyl acetate:dichloromethane:hexane=10:10:80) to give the title compound (3.15 g, 7.93 mmol, 63%) as yellow crystals.
Nuclear magnetic resonance spectrum (CDCl$_3$, TMS internal standard)
δ: 3.36 (3H, s), 6.75 (1H, d), 6.79 (1H, d), 6.93 (1H, m), 7.10–7.15 (2H, m), 7.30–7.35 (3H, m).

Reference Example 25
2-Bromomethyl-9H-xanthen-9-one
Benzoyl peroxide (4.6 g, 19 mmol) and N-bromosuccinimide (67.6 g, 380 mmol) were added to a mixture of 2-methyl-9H-xanthen-9-one (79.9 g, 380 mmol) and carbon tetrachloride (800 ml) with heating under reflux, and the mixture was stirred for 4 hours. After spontaneous cooling to room temperature, water was added to the reaction mixture, and the reaction product was extracted with chloroform. The extract was washed with saturated sodium bicarbonate aqueous solution, water and saturated sodium chloride aqueous solution in that order, dried over anhydrous magnesium sulfate, and then concentrated under a reduced pressure. The resulting residue was recrystallized from ethyl acetate to give the title compound (78.3 g, 271 mmol, 71%) as yellow crystals.
Nuclear magnetic resonance spectrum (CDCl$_3$, TMS internal standard)

δ: 4.61 (2H, s), 7.39 (1H, m), 7.45–7.50 (2H, m), 7.65–7.75 (2H, m), 8.30–8.35 (2H, m).

Reference Example 26
Borane-[3-(10-methylphenothiazin-3-ylmethoxy) quinuclidine] complex In an atmosphere of argon, sodium hydride (60 wt. %, 1.16 g, 29 mmol) was added to a mixture of borane-(3-quinuclidinol) complex (3.38 g, 24 mmol) and DMF (35 ml), and the mixture was stirred for 1 hour. With ice-cooling, a DMF (30 ml) solution of 3-chloromethyl-10-methylphenothiazine (7.98 g, 30.5 mmol) was added to the reaction mixture, and the mixture was stirred for 30 minutes and then at room temperature for 30 minutes. Water was added to the reaction mixture and the reaction product was extracted with ethyl acetate. The extract was washed with water and saturated sodium chloride aqueous solution in that order, dried over anhydrous magnesium sulfate, and then concentrated under a reduced pressure. The resulting residue was purified by silica gel column chromatography (eluent; ethyl acetate:dichloromethane:hexane=10:10:80, then 15:15:70) to give the title compound (5.09 g, 13.9 mmol, 58%) as yellow foam.

Nuclear magnetic resonance spectrum (CDCl$_3$, TMS internal standard)
δ: 1.55–1.65 (2H, m), 1.83 (1H, m), 2.07 (1H, m), 2.02 (1H, m), 2.85–3.00 (4H, m), 3.05 (1H, m), 3.18 (1H, m), 3.37 (3H, s), 3.67 (1H, m), 4.37 (1H, d), 4.41 (1H, d), 6.78 (1H, d), 6.81 (1H, d), 6.93 (1H, m), 7.05–7.20 (4H, m).

The compound of Reference Example 27 was obtained in the same manner as in Reference Example 26.

Reference Example 27
Borane-[10-methyl-3-(3-quinuclidinyloxymethyl) phenothiazine-5-oxide] complex Material compounds: 3-chloromethyl-10-methylphenothiazine-5-oxide and borane-(3-quinuclidinol) complex Nuclear magnetic resonance spectrum (CDCl$_3$, TMS internal standard)
δ: 1.60–1.65 (2H, m), 1.86 (1H, m), 2.09 (1H, m), 2.27 (1H, m), 2.85–3.00 (4H, m), 3.07 (1H, m), 3.23 (1H, m), 3.74 (1H, m), 3.77 (3H, s), 4.50–4.60 (2H, m), 7.25 (1H, m), 7.35–7.40 (2H, m), 7.56 (1H, m), 7.63 (1H, m), 7.86 (1H, m), 7.92 (1H, m).

Reference Example 28
Borane-[3-(10-ethylphenothiazin-3-ylmethoxy) quinuclidine] complex In an atmosphere of argon, thionyl chloride (0.65 ml, 8.86 mmol) was added at 0° C. to a mixture of 10-ethyl-3-hydroxymethylphenothiazine (1.14 g, 4.43 mmol), DMF (0.1 ml) and methylene chloride (12 ml), and the mixture was stirred for 1 hour and then at room temperature for 1 hour. The reaction mixture was concentrated under a reduced pressure, and chloroform and a saturated sodium bicarbonate aqueous solution (each 20 ml) were added to the residue in that order. The reaction product was extracted with ethyl acetate, and the extract was washed with saturated sodium chloride aqueous solution. The extract was dried over anhydrous magnesium sulfate, and then concentrated under a reduced pressure to give 3-chloromethyl-10-ethylphenothiazine (1.17 g, 4.24 mmol, 96%) as brown oil.

In an atmosphere of argon, sodium hydride (60 wt. %, 195 mg, 4.43 mmol) was added at 0° C. to a mixture of borane-(3-quinuclidinol) complex (558 mg, 4.43 mmol) and DMF (8 ml), and the mixture was stirred for 30 minutes. A mixture of 3-chloromethyl-10-ethylphenothiazine (1.17 g, 4.24 mmol) and DMF (4 ml) were added, and the mixture was again stirred for 1 hour. The reaction mixture was concentrated under a reduced pressure, ethyl acetate and saturated sodium chloride aqueous solution (each 30 ml) were added to the residue in that order, and the reaction product was extracted with ethyl acetate. The extract was dried over anhydrous magnesium sulfate and then concentrated under a reduced pressure. The resulting residue was purified by silica gel column chromatography (eluent; hexane:ethyl acetate=3:1) to give the title compound (1.28 g, 3.37 mmol, 79%) as yellow oil.

Nuclear magnetic resonance spectrum (CDCl$_3$, TMS internal standard)
δ: 0.98 (3H, brs), 1.18–2.30 (8H, m), 2.81–3.18 (6H, m), 3.60–3.74 (1H, m), 3.92 (2H, q, J=7 Hz), 4.37 (2H, s), 6.76–7.25 (7H, m).

The compounds of Reference Examples 29 to 31 were obtained in the same manner as in Reference Example 28.

Reference Example 29
Borane-[3-(10-butylphenothiazin-3-ylmethoxy) quinuclidine] complex Material compounds: 3-hydroxymethyl-10-butylphenothiazine, borane-(3-quinuclidinol) complex Nuclear magnetic resonance spectrum (CDCl$_3$, TMS internal standard)
δ: 0.75–1.04 (6H, m), 1.19–1.91 (8H, m), 2.15–2.30 (1H, m), 2.71–3.17 (6H, m), 3.86 (2H, t, J=8 Hz), 3.91–4.16 (1H, m), 4.39 (2H, s), 6.79–7.36 (7H, m).

Reference Example 30
Borane-[3-[10-(1-methylethyl)phenothiazin-3-ylmethoxy] quinuclidine] complex Material compounds: 3-hydroxymethyl-10-(1-methylethyl)phenothiazine, borane-(3-quinuclidinol) complex Nuclear magnetic resonance spectrum (CDCl$_3$, TMS internal standard)
δ: 0.90 (3H, brs), 1.12–1.35 (4H, m), 2.15–2.30 (1H, m), 2.71–3.17 (6H, m), 3.86 (2H, t, J=8 Hz), 3.91–4.16 (1H, m), 4.39 (2H, s), 6.79–7.36 (7H, m).

Reference Example 31
Borane-[3-(3-chloro-10-methylphenoxazin-7-ylmethoxy) quinuclidine] complex Material compounds: 3-hydroxymethyl-10-methylphenoxazine, borane-(3-quinuclidinol) complex Nuclear magnetic resonance spectrum (CDCl$_3$, TMS internal standard)
δ: 0.85 (3H, brs), 1.48–1.98 (3H, m), 2.01–2.27 (2H, m), 2.79–3.20 (9H, m), 3.60–3.80 (1H, m), 4.32 (2H, s), 6.34–6.83 (6H, m).

Reference Example 32
Borane-[(9H-xanthen-9-on-3-ylmethoxy)quinuclidine] complex

A mixture of 3-methyl-9H-xanthen-9-one (1.62 g, 7.71 mmol), N-bromosuccinic acid imide (1.37 g, 7.71 mmol), benzoyl peroxide (93 mg, 0.39 mmol) and carbon tetrachloride (15 ml) was heated under reflux for 15 hours. The insoluble matter was removed by filtration and the resulting filtrate was concentrated under a reduced pressure to give 3-bromomethyl-9H-xanthen-9-one (2.19 g, 7.57 mmol, 98%) as colorless crystals.

In an atmosphere of argon, sodium hydride (60 wt. %, 339 mg, 7.71 mmol) was added at 0° C. to a mixture of borane-[3-hydroxyquinuclidine] complex (1.20 g, 7.71 mmol) and DMF (15 ml), and the resulting mixture was stirred for 30 minutes. A mixture of 3-bromomethyl-9H-xanthen-9-one (2.19 g, 7.57 mmol) and DMF (8 ml) were added, and the mixture was again stirred for 1 hour. The reaction mixture was concentrated under a reduced pressure, ethyl acetate and saturated sodium chloride aqueous solution (each 50 ml) were added to the resulting residue in that order, and then the reaction product was extracted with ethyl acetate. The extract was dried over anhydrous magnesium sulfate and then concentrated under a reduced pressure. The resulting residue was purified by silica gel column chromatography (eluent; hexane:ethyl acetate=3:2) to give the title compound (260 mg, 0.74 mmol, 9.7%) as colorless crystals.

Nuclear magnetic resonance spectrum (CDCl$_3$, TMS internal standard)

δ: 0.92 (3H, brs), 1.18–1.35 (1H, m), 1.51–1.96 (2H, m), 1.98–2.38 (2H, m), 2.85–3.29 (6H, m), 3.73–3.90 (1H, m), 4.64 (2H, s), 7.21–7.85 (4H, m), 8.23–8.36 (2H, m).

The compound of Reference Example 33 was obtained in the same manner as in Reference Example 32.

Reference Example 33

Borane-[(9H-xanthen-9-on-1-ylmethoxy)quinuclidine] complex

Material compounds: 1-methyl-9H-xanthen-9-one, borane-(3-quinuclidinol) complex

Nuclear magnetic resonance spectrum (CDCl$_3$, TMS internal standard)

δ: 0.88 (3H, brs), 1.16–1.35 (2H, m), 1.60–1.90 (2H, m), 2.38–2.55 (1H, m), 2.89–3.35 (6H, m), 3.85–4.04 (1H, m), 5.24 (1H, d, J=12 Hz), 5.38 (1H, d, J=12 Hz), 7.35–7.56 (3H, m), 7.60–7.83 (3H, m), 8.23 (1H, dd, J=2 Hz, 8 Hz).

Reference Example 34

Borane-[(Z)-3-[2-(9H-xanthen-9-on-2-ylmethoxy)ethylidene]quinuclidine] complex

In an atmosphere of argon, sodium hydride (60 wt. %, 359 mg, 8.98 mmol) was added at 0° C. to a mixture of borane-[(Z)-3-(2-hydroxyethylidene)quinuclidine] complex (1.50 g, 8.98 mmol) and DMF (17 ml), and the resulting mixture was stirred for 30 minutes. 2-Bromomethyl-9H-xanthen-9-one (1.39 g, 8.98 mmol) was added, and the mixture was again stirred for 2 hours. The reaction mixture was concentrated under a reduced pressure, ethyl acetate and saturated sodium chloride aqueous solution (each 50 ml) were added to the resulting residue in that order, and then the reaction product was extracted with ethyl acetate. The extract was dried over anhydrous magnesium sulfate and then concentrated under a reduced pressure. The resulting residue was purified by silica gel column chromatography (eluent; hexane:ethyl acetate=1:1) to give the title compound (970 mg, 2.58 mmol, 29%) as colorless crystals.

Nuclear magnetic resonance spectrum (CDCl$_3$, TMS internal standard)

δ: 0.90 (3H, brs), 1.76–1.97 (4H, m), 2.48–2.62 (1H, m), 2.97–3.15 (4H, m), 3.65 (2H, s), 3.97 (2H, d, J=7 Hz), 4.62 (2H, s), 5.42–5.62 (1H, m), 7.37–7.82 (5H, m), 8.27–8.40 (2H, m).

The compound of Reference Example 35 was obtained in the same manner as in Reference Example 34.

Reference Example 35

Borane-[(Z)-3-[2-(10-methylphenothiazin-3-ylmethoxy)ethylidene]quinuclidine] complex Material compound: 3-chloromethyl-10-methylphenothiazine, borane-[(Z)-3-(2-hydroxyethylidene)quinuclidine] complex Nuclear magnetic resonance spectrum (CDCl$_3$, TMS internal standard)

δ: 1.08 (3H, brs), 1.82–2.10 (4H, m), 2.51–2.64 (1H, m), 3.05–3.29 (4H, m), 3.47 (3H, s), 3.76 (2H, s), 4.01 (2H, d, J=6 Hz), 4.53 (2H, s), 5.47–5.72 (1H, m), 6.86–7.33 (7H, m).

Reference Example 36

Borane-[(Z)-3-(1-fluoro-2-hydroxyethylidene)quinuclidine] complex

With ice-cooling, sodium diisobutyl aluminum hydride (1.01M toluene solution, 634 ml, 640 mmol) was added dropwise to a mixture of borane-[ethyl (Z)-fluoro-(3-quinuclidinylidene)acetate] complex (66.1 g, 291 mmol, E/Z mixture) and toluene (200 ml) spending 1.5 hours, and the mixture was stirred for 0.5 hour. Methanol (60 ml), ethyl acetate (500 ml) and water (500 ml) were added to the reaction mixture in that order and the mixture was stirred at room temperature. The insoluble matter was removed by filtration and the reaction product was extracted with ethyl acetate. The extract was washed with saturated sodium chloride aqueous solution, dried over anhydrous magnesium sulfate, and then concentrated under a reduced pressure. The resulting residue was purified by silica gel column chromatography (eluent; ethyl acetate:dichloromethane:hexane= 20:10:70, then 30:10:60) to give the title compound (10.0 g, 54 mmol, 19%) and borane-[(E)-3-(1-fluoro-2-hydroxyethylidene)quinuclidine] complex (25.4 g, 47%), both as colorless crystals.

Nuclear magnetic resonance spectrum (CDCl$_3$, TMS internal standard)

δ: 1.30–1.80 (3H, br), 1.80–1.95 (5H, m), 1.99 (1H, m), 3.00–3.15 (4H, m), 3.67 (2H, s), 4.13 (2H, m).

The compound of Reference Example 37 was obtained in the same manner as in Reference Example 4.

Reference Example 37

Borane-[(Z)-3-[2-(carbazol-2-yloxy)-1-fluoroethylidene]quinuclidine] complex

Material compounds: borane-[(Z)-3-(1-fluoro-2-hydroxyethylidene)quinuclidine] complex, 2-hydroxycarbazole Nuclear magnetic resonance spectrum (DMSO-d$_6$, TMS internal standard)

δ: 1.65–1.96 (4H, m), 2.72–3.12 (5H, m), 3.75 (2H, d, J=21 Hz), 6.78–6.97 (2H, m), 7.09–7.41 (3H, m), 7.70–8.03 (2H, m).

The compound of Reference Example 38 was obtained in the same manner as in Reference Example 25.

Reference Example 38

4-Bromomethyl-9H-xanthen-9-one

Material compound: 4-methyl-9H-xanthen-9-one

Nuclear magnetic resonance spectrum (CDCl$_3$, TMS internal standard)

δ: 4.84 (2H, s), 7.35–7.45 (2H, m), 7.61 (1H, d, J=9 Hz), 7.76–7.80 (2H, m), 8.33–8.37 (2H, m).

Reference Example 40

2-Hydroxy-9H-xanthen-9-one

Boron tribromide (1.0M dichloromethane solution, 50 ml, 50 mmol) was added to a mixture of 2-methoxy-9H-xanthen-9-one (5.66 g, 25.0 mmol) and dichloromethane (50 ml), and the mixture was stirred for 3 hours. The reaction mixture was poured into ice water and the reaction product was extracted with chloroform. The extract was washed with water and saturated sodium chloride aqueous solution in that order, dried over anhydrous magnesium sulfate, and then concentrated under a reduced pressure to give the title compound (5.00 g, 23.6 mmol, 94%) as yellow crystals.

Nuclear magnetic resonance spectrum (DMSO-$d_6$, TMS internal standard)

δ: 7.30–7.40 (3H, m), 7.48 (1H, d), 7.70–7.75 (2H, m), 8.30 (1H, m), 9.20 (1H, s).

Example 1

1) (E)-3-[2-(Carbazol-2-yloxy)-1-fluoroethylidene] quinuclidine

After dissolving borane-[(E)-3-(2-chloro-1-fluoroethylidene)quinuclidine] complex (106.5 g, 304 mmol) in acetone (2.3 l) while heating under reflux, a hydrogen chloride ethanol solution (about 5M, 300 ml) was added to the resulting solution while cooling with ice-water both spending 5 minutes (inner temperature, 18° to 23° C.). The reaction mixture was stirred at room temperature for 1 hour, diluted with diethyl ether (2.0 l), and then the thus precipitated crystals were collected by filtration and dried. The resulting crystals were added to a mixture of potassium carbonate (200 g), water (800 ml) and chloroform (1.2 l), the mixture was stirred at 50° C. for 1 hour, and the crystals were collected by filtration (72.1 g). They were combined with other portion of crystals (22.2 g) obtained by extraction of the filtrate with chloroform, and the combined crystals, 94.1 g in total; were recrystallized from dioxane to give the title compound 84.5 g, 251 mmol, 83%).

Nuclear magnetic resonance spectrum (CDCl$_3$, TMS internal standard)

δ: 1.60–1.70 (4H, m), 2.81 (2H, m), 2.90 (2H, m), 3.02 (1H, m), 3.52 (2H, d), 4.60 (2H, d), 6.90 (1H, dd), 6.97 (1H, d), 7.21 (1H, m), 7.30–7.40 (2H, m), 7.95 (1H, d), 7.98 (1H, d), 8.09 (1H, brs).

2) (E)-3-[2-(Carbazol-2-yloxy)-1-fluoroethylidene] quinuclidine hydrochloride

After dissolving (E)-3-[2-(carbazol-2-yloxy)-1-fluoroethylidene]quinuclidine (95.5 g, 284 mmol) in ethanol (7.0 l) while heating under reflux, a hydrogen chloride ethanol solution (about 5M, 90 ml) was added to the resulting solution with ice-cooling, spending 3 minutes. After additional 0.5 hour of ice-cooling, the thus precipitated crystals were collected by filtration and dried to give the title compound (85.2 g, 228 mmol, 80%).

Melting point: 241°–243° C.

Nuclear magnetic resonance spectrum (DMSO-$d_6$, TMS internal standard)

δ: 1.80–1.86 (2H, m), 1.95–2.02 (2H, m), 3.14–3.33 (4H, m), 4.10 (2H, s), 4.76 (2H, d, J=20 Hz), 6.82–6.84 (1H, m), 7.03–7.04 (1H, m), 7.10–7.13 (1H, m), 7.28–7.32 (1H, m), 7.44–7.47 (1H, m), 7.79–8.01 (2H, m), 10.85 (1H, brs), 11.25 (1H, brs).

The following compounds of Examples 2 to 5 were obtained in the same manner as in Example 1.

Example 2

(Z)-3-[2-(Carbazol-2-yloxy)ethylidene]quinuclidine hydrochloride

Material compound: borane-[(Z)-3-[2-(carbazol-2-yloxy) ethylidene]quinuclidine] complex Melting point: 251°–253° C.

Nuclear magnetic resonance spectrum (DMSO-$d_6$, TMS internal standard)

δ: 1.80–1.88 (2H, m), 1.93–2.02 (2H, m), 2.70–2.74 (1H, m), 3.22–3.32 (4H, m), 4.14 (2H, s), 4.60 (2H, d, J=7 Hz), 5.74–5.76 (1H, m), 6.76–6.80 (1H, m), 6.98–7.00 (1H, m), 7.10–7.14 (1H, m), 7.28–7.32 (1H, m), 7.62 (1H, d, J=8 Hz), 7.94–8.00 (2H, m), 10.54 (1H, brs), 11.17 (1H, brs).

Example 3

(Z)-3-[2-(Carbazol-2-yloxy)-1-methylethylidene] quinuclidine hydrochloride

Material compound: borane-[(Z)-3-[2-(carbazol-2-yloxy)-1-methylethylidene]quinuclidine] complex Melting point: 259°–262° C.

Nuclear magnetic resonance spectrum (DMSO-$d_6$, TMS internal standard)

δ: 1.74–1.82 (5H, m), 1.92–2.00 (2H, m), 3.03–3.04 (1H, m), 3.21–3.29 (4H, m), 4.08 (2H, s), 4.51 (2H, s), 6.78–6.81 (1H, m), 6.99 (1H, s), 7.09–7.12 (1H, m), 7.27–7.30 (1H, m), 7.43 (1H, d, J=8 Hz), 7.96–8.00 (2H, m), 10.73 (1H, brs).

Example 4

Ethyl (z)-[2-[2-(3-quinuclidinylidene)ethoxy]carbazol-9-yl] acetate hydrochloride Material compound: borane-[ethyl (Z)-[2-[2-(3-quinuclidinylidene)ethoxy]carbazol-9-yl]acetate] complex Melting point: 138°–141° C.

Nuclear magnetic resonance spectrum (DMSO-$d_6$, TMS internal standard)

δ: 1.21 (3H, t, J=7 Hz), 1.78–1.88 (2H, m), 1.82–2.00 (2H, m), 2.68–2.70 (1H, m), 3.20–3.31 (4H, m), 4.11 (2H, s), 4.16 (2H, q, J=7 Hz), 4.62 (2H, d, J=7 Hz), 5.29 (2H, s), 5.72–5.76 (1H, m), 6.84–6.86 (1H, m), 7.14–7.20 (2H, m), 7.33–7.36 (1H, m), 7.45 (1H, d, J=8 Hz), 8.01–8.04 (2H, m), 10.61 (1H, brs).

Example 5

(Z)-3-[2-[9-(2-Aminoethyl)carbazol-2-yloxy]ethylidene] quinuclidine dihydrochloride Material compound: borane-[(Z)-3-[2-[9-(2-aminoethyl) carbazol-2-yloxy]ethylidene]quinuclidine] complex Melting point: 244°–250° C.

Nuclear magnetic resonance spectrum (DMSO-$d_6$, TMS internal standard)

δ: 1.80–1.88 (2H, m), 1.92–2.00 (2H, m), 2.68–2.71 (1H, m), 3.16–3.22 (2H, m), 3.26–3.33 (4H, m), 4.12 (2H, s), 4.69–4.73 (4H, m), 5.76–5.78 (1H, m), 6.85 (1H, d, J=7 Hz), 7.18–7.21 (1H, m), 7.37–7.40 (1H, m), 7.48 (1H, s), 7.64 (1H, s), 8.01–8.06 (2H, m), 8.49 (3H, brs), 10.82 (1H, brs).

Example 6

(Z)-3-[2-(9-Methylcarbazol-2-yloxy)ethylidene] quinuclidine hydrochloride

In an atmosphere of argon, sodium hydride (60 wt. %, 0.15 g, 3.83 mmol) was added at 0° C. to a mixture of borane-[(Z)-3-[2-(9-methylcarbazol-2-yloxy)ethylidene] quinuclidine] complex (1.06 g, 3.19 mmol) and DMF (9 ml), and the resulting mixture was stirred for 30 minutes. Methyl iodide (0.24 ml, 3.83 mmol) was added, and the mixture was again stirred for 1 hour. The reaction mixture was concentrated under a reduced pressure, ethyl acetate and saturated sodium chloride aqueous solution (each 20 ml) were added to the resulting residue in that order, and the reaction product was extracted with ethyl acetate. Then, the extract was dried over anhydrous magnesium sulfate and concentrated under a reduced pressure to give colorless crystals (1.22 g). To a mixture thereof with acetone (25 ml) was added a hydrogen chloride ethanol solution (about 5M, 5 ml) at room temperature, and the resulting mixture was stirred for 30 minutes and then diluted with diethyl ether (25 ml). The precipitate was collected by filtration and dried under a reduced pressure to give the title compound (1.10 g, 2.98 mmol, 93%) as colorless crystals.

Melting point: 241°–244° C.

Nuclear magnetic resonance spectrum (DMSO-$d_6$, TMS internal standard)

δ: 1.82–1.88 (2H, m), 1.94–2.00 (2H, m), 2.71–2.72 (1H, m), 3.21–3.27 (4H, m), 3.84 (3H, s), 4.12 (2H, s), 4.66 (2H, d, J=6 Hz), 5.77–5.79 (1H, m), 6.82–6.84 (1H, m), 7.15–7.17 (1H, m), 7.36–7.39 (1H, m), 7.52–7.53 (1H, m), 8.01–8.04 (2H, m), 10.87 (1H, brs).

The following compounds of Examples 7 to 10 were obtained in the same manner as in Example 6.

Example 7

(Z)-3-[2-(9-Butylcarbazol-2-yloxy)ethylidene]quinuclidine hydrochloride

Material compounds: borane-[(Z)-3-[2-(carbazol-2-yloxy)ethylidene]quinuclidine] complex, butyl iodide Melting point: 202°–204° C.

Nuclear magnetic resonance spectrum (DMSO-$d_6$, TMS internal standard)

δ: 0.89 (3H, t, J=7 Hz), 1.27–1.35 (2H, m), 1.71–1.77 (2H, m), 1.80–1.84 (2H, m), 1.94–2.00 (2H, m), 2.70–2.72 (1H, m), 3.21–3.34 (4H, m), 4.13 (2H, s), 4.35 (2H, t, J=7 Hz), 5.76–5.78 (1H, m), 6.81–6.83 (1H, m), 7.12–7.16 (1H, m), 7.34–7.37 (1H, m), 7.52 (1H, d, J=9 Hz), 8.00–8.03 (2H, m), 10.81 (1H, brs).

Example 8

(Z)-3-[2-(9-Benzylcarbazol-2-yloxy)ethylidene]quinuclidine hydrochloride

Material compounds: borane-[(Z)-3-[2-(carbazol-2-yloxy)ethylidene]quinuclidine] complex, benzyl bromide Melting point: 220°–222° C.

Nuclear magnetic resonance spectrum (DMSO-$d_6$, TMS internal standard)

δ: 1.74–1.82 (2H, m), 1.90–1.98 (2H, m), 2.66–2.70 (1H, m), 3.16–3.24 (2H, m), 3.28–3.34 (2H, m), 4.10 (2H, s), 4.60 (2H, d, J=6 Hz), 5.63 (2H, s), 5.72–5.74 (1H, m), 6.85 (1H, dd, J=2 Hz, 9 Hz), 7.15–7.34 (8H, m), 7.52 (1H, d, J=9 Hz), 8.04–8.07 (2H, m), 10.48 (1H, brs).

Example 9

(Z)-3-[2-[9-[2-(dimethylamino)ethyl]carbazol-2-yloxy]ethylidene]quinuclidine dihydrochloride Material compounds: borane-[(Z)-3-[2-(carbazol-2-yloxy)ethylidene]quinuclidine] complex, 2-dimethylaminoethyl chloride hydrochloride, sodium iodide Melting point: 213°–216° C.

Nuclear magnetic resonance spectrum (DMSO-$d_6$, TMS internal standard)

δ: 1.80–1.90 (2H, m), 1.94–2.04 (2H, m), 2.71–2.73 (1H, m), 2.85 (6H, s), 3.26–3.33 (4H, m), 3.40 (2H, t, J=7 Hz), 4.15 (2H, s), 4.85 (2H, t, J=7 Hz), 5.78–5.81 (1H, m), 6.87 (1H, d, J=8 Hz), 7.18–7.22 (1H, m), 7.38–7.42 (1H, m), 7.51 (1H, s), 7.72 (1H, d, J=8 Hz), 8.03–8.06 (2H, m), 10.76 (1H, brs), 11.67 (1H, brs).

Example 10

(Z)-[2-[2-(3-quinuclidinylidene)ethoxy]carbazol-9-yl]acetamide hydrochloride

Material compounds: borane-[(Z)-3-[2-(carbazol-2-yloxy)]ethylidene]quinuclidine] complex, chloroacetamide, sodium iodide Melting point: 252°–255° C.

Nuclear magnetic resonance spectrum (DMSO-$d_6$, TMS internal standard)

δ: 1.78–1.88 (2H, m), 1.92–2.00 (2H, m), 2.68–2.72 (1H, m), 3.12–3.35 (4H, m), 4.12 (2H, s), 4.64 (2H, d, J=6 Hz), 4.96 (2H, s), 5.70–5.76 (1H, m), 6.84 (1H, d, J=9 Hz), 7.10 (1H, s), 7.11–7.18 (1H, m), 7.27 (1H, s), 7.33–7.36 (1H, m), 7.43 (1H, d, J=8 Hz), 7.73 (1H, s), 8.02 (2H, t, J=8 Hz), 10.73 (1H, brs).

Example 11

(Z)-3-[2-[9-(2-Methoxyethyl)carbazol-2-yloxy]ethylidene]quinuclidine

At 0° C., a hydrogen chloride ethanol solution (about 5M, 0.5 ml) was added to a mixture of borane-[(Z)-3-[2-[9-(2-hydroxyethyl)carbazol-2-yloxy]ethylidenequinuclidine]] complex (540 mg, 1.38 mmol) and acetone (2.6 ml), and the mixture was stirred for 30 minutes. Triethylamine (1 ml) was added to the reaction mixture, and the mixture was concentrated under a reduced pressure. Chloroform and a 2N sodium hydroxide aqueous solution (each 10 ml) were added to the resulting residue in that order. The reaction product was extracted with chloroform. The extract was dried over anhydrous magnesium sulfate and concentrated under a reduced pressure. The resulting residue was purified by silica gel column chromatography (eluent; chloroform::methanol:17% aqueous ammonia=100:3:0.3) and then recrystallized from diethyl ether to give the title compound (440 mg, 1.17 mmol, 85%) as colorless crystals.

Melting point: 90°–91° C.

Nuclear magnetic resonance spectrum (CDCl$_3$, TMS internal standard)

δ: 1.64–1.67 (4H, m), 2.35–2.36 (1H, m), 2.62–2.68 (2H, m), 2.75–2.81 (2H, m), 3.56 (2H, s), 4.01 (2H, t, J=5 Hz), 4.39 (2H, t, J=5 Hz), 4.49 (2H, d, J=6 Hz), 5.47–5.49 (1H, m), 6.83–6.85 (1H, m), 6.96 (1H, s), 7.18–7.21 (1H, m), 7.36–7.43 (2H, m), 7.34–7.99 (2H, m).

Example 12

The following compound of Example 12 was obtained in the same manner as in Example 11.

(Z)-3-[2-[9-(2-Hydroxyethyl)carbazol-2-yloxy]ethylidene]quinuclidine

Material compound: borane-[(Z)-3-[2-[9-(2-hydroxyethyl)carbazol-2-yloxy]]ethylidene]quinuclidine] complex Melting point: 146°–148° C.

Nuclear magnetic resonance spectrum (CDCl$_3$, TMS internal standard)

δ: 1.73–1.76 (4H, m), 2.42–2.43 (1H, m), 2.85–2.97 (4H, m), 3.31 (3H, s), 3.64 (2H, s), 3.76 (2H, t, J=6 Hz), 4.42 (2H, t, J=6 Hz), 4.59 (2H, d, J=6 Hz), 5.55–5.57 (1H, m), 6.88 (1H, dd, J=9 Hz), 6.94 (1H, s), 7.18–7.21 (1H, m), 7.36–7.39 (2H, m), 7.93–7.98 (2H, m).

Example 13

3-(9H-Xanthen-9-on-2-ylmethoxy)quinuclidine hydrochloride

In an atmosphere of argon, sodium hydride (60 wt. %, 69 mmol) was added to a DMF (100 ml) solution of borane-(3-quinuclidinol) complex (8.46 g, 60 mmol), and the mixture was stirred for 30 minutes and then cooled with ice. 2-Bromomethyl-9H-xanthen-9H-one (19.1 g, 66 mmol) was added to the reaction mixture, and the mixture was stirred for 1 hour. Then, water was added, and the reaction product was extracted with chloroform. The extract was washed with water and saturated sodium chloride aqueous solution in that order, dried over anhydrous magnesium sulfate, and then concentrated under a reduced pressure. Acetone (150 ml) and a hydrogen chloride ethanol solution (ca. 5M, 60 ml) were added to the resulting residue in that order, and the mixture was stirred for 20 minutes and then concentrated under a reduced pressure. A potassium carbonate-aqueous solution (ca. 30 wt. %, 280 g) was added to the residue. The reaction product was extracted with chloroform, dried over anhydrous magnesium sulfate, and then concentrated under a reduced pressure. The resulting yellow oil was purified by silica gel column chromatography (eluent; 29% aqueous ammonia:methanol:chloroform=1:10:90) to give 3-(9H-xanthen-9-on-2-ylmethoxy)quinuclidine as yellow oil. This was dissolved in ethyl acetate (100 ml), 4N hydrogen chloride-ethyl acetate (7.5 ml) was added, and the thus precipitated crystals were collected by filtration to give the title compound (9.05 g, 24.3 mmol, 41%) as colorless crystals.

Elemental analysis (for $C_{21}H_{21}NO_3$)

|  | C (%) | H (%) | N (%) | Cl (%) |
|---|---|---|---|---|
| Calcd. | 67.83 | 5.96 | 3.77 | 9.53 |
| Found | 67.69 | 5.99 | 3.77 | 9.74 |

Nuclear magnetic resonance spectrum (DMSO-$d_6$, TMS internal standard)

δ: 1.70–1.75 (2H, m), 1.91 (1H, m), 2.05 (1H, m), 2.40 (1H, m), 3.05–3.25 (5H, m), 3.55 (1H, m), 4.00 (1H, m), 4.66 (1H, d), 4.70 (1H, d), 7.49 (1H, dd), 7.65–7.70 (2H, m), 7.85–7.95 (2H, m), 8.15–8.25 (2H, m), 10.80 (1H, brs).

The following compounds of Examples 14 to 16 were obtained in the same manner as Example 13.

Example 14
(R)-3-(9H-Xanthen-9-on-2-ylmethoxy)quinuclidine hydrochloride

Material compounds: 2-bromomethyl-9H-xanthen-9-one, borane-[(R)-3-quinuclidinol] complex Mass spectrometry data (m/z): 335 (M$^+$)

Nuclear magnetic resonance spectrum (DMSO-$d_6$, TMS internal standard)

δ: 1.65–1.75 (2H, m), 1.90 (1H, m), 2.04 (1H, m), 2.40 (1H, m), 3.05–3.20 (5H, m), 3.55 (1H, m), 3.99 (1H, m), 4.66 (1H, d), 4.70 (1H, d), 7.50 (1H, dd), 7.65–7.70 (2H, m), 7.85–7.95 (2H, m), 8.15–8.25 (2H, m), 10.45 (1H, brs).

Example 15
(S)-3-(9H-Xanthen-9-on-2-ylmethoxy)quinuclidine hydrochloride

Material compounds: 2-bromomethyl-9H-xanthen-9-one, borane-[(S)-3-quinuclidinol] complex Mass spectrometry data (m/z): 335 (M$^+$)

Nuclear magnetic resonance spectrum (DMSO-$d_6$, TMS internal standard)

δ: 1.70–1.75 (2H, m), 1.91 (1H, m), 2.05 (1H, m), 3.05–3.20 (5H, m), 3.55 (1H, m), 3.99 (1H, m), 4.66 (1H, d), 4.70 (1H, d), 7.50 (1H, dd), 7.65–7.70 (2H, m), 7.85–7.95 (2H, m), 8.15–8.25 (2H, m), 10.66 (1H, brs).

Example 16
10-Methyl-3-(3-quinuclidinyloxymethyl)phenothiazine-5,5-dioxide hydrochloride Material compounds: 3-chloromethyl-10-methylphenothiazine-5,5-dioxide, borane-(3-quinuclidinol) complex Melting point: 274°–276° C.

Nuclear magnetic resonance spectrum (DMSO-$d_6$, TMS internal standard)

δ: 1.65–1.70 (2H, m), 1.90 (1H, m), 2.01 (1H, m), 2.37 (1H, m), 3.05–3.20 (5H, m), 3.51 (1H, m), 3.74 (3H, s), 3.95 (1H, m), 4.61 (1H, d), 4.65 (1H, d), 7.37 (1H, dd), 7.60–7.65 (2H, m), 7.75–7.80 (2H, m), 7.95–8.00 (2H, m), 10.34 (1H, brs).

Example 17
3-(10-Methylphenothiazin-3-ylmethoxy)quinuclidine hydrochloride

With ice-cooling, a hydrogen chloride ethanol solution (ca. 5M, 10 ml) was added to an acetone (20 ml) solution of borane-[3-(10-methylphenothiazin-3-ylmethoxy)quinuclidine] complex (5.09 g, 13.9 mmol), and the mixture was stirred for 5 minutes and then diluted with diethyl ether (40 ml). The resulting precipitate was collected by filtration and dried under a reduced pressure to give the title compound (4.48 g, 11.5 mmol, 83%) as light green crystals.

Melting point: 220°–222° C.

Nuclear magnetic resonance spectrum (DMSO-$d_6$, TMS internal standard)

δ: 1.65–1.70 (2H, m), 1.87 (1H, m), 1.98 (1H, m), 2.31 (1H, m), 2.95–3.15 (5H, m), 3.31 (3H, s), 3.47 (1H, m), 3.86 (1H, m), 4.39 (1H, d), 4.44 (1H, d), 6.90–7.00 (3H, m), 7.15–7.25 (4H, m).

The following compounds of Examples 18 to 22 were obtained in the same manner as Example 17.

Example 18
(R)-3-(10-Methylphenothiazin-3-ylmethoxy)quinuclidine hydrochloride Material compound: borane-[(R)-3-(10-methylphenothiazin-3-ylmethoxy)quinuclidine] complex Melting point: 220°–221° C.

Nuclear magnetic resonance spectrum (DMSO-$d_6$, TMS internal standard)

δ: 1.65–1.70 (2H, m), 1.87 (1H, m), 1.98 (1H, m), 2.31 (1H, m), 3.00–3.20 (5H, m), 3.31 (3H, s), 3.47 (1H, m), 3.87 (1H, m), 4.39 (1H, d), 4.44 (1H, d), 6.90–7.00 (3H, m), 7.15–7.25 (4H, m).

Example 19
(S)-3-(10-Methylphenothiazin-3-ylmethoxy)quinuclidine hydrochloride Material compound: borane-[(S)-3-(10-methylphenothiazin-3-ylmethoxy)quinuclidine] complex Melting point: 214°–217° C.

Nuclear magnetic resonance spectrum (CDCl$_3$, TMS internal standard)

δ: 1.60–1.70 (2H, m), 1.88 (1H, m), 1.98 (1H, m), 2.30 (1H, m), 3.00–3.20 (5H, m), 3.31 (3H, s), 3.46 (1H, m), 3.87 (1H, m), 4.39 (1H, d), 4.44 (1H, d), 6.90–7.00 (3H, m), 7.15–7.25 (4H, m).

Example 20
3-(9H-Xanthen-9-on-3-ylmethoxy)quinuclidine hydrochloride

Material compound: borane-[3-(9H-xanthen-9-on-3-ylmethoxy)quinuclidine] complex

Melting point: 246°–248° C.

Nuclear magnetic resonance spectrum (DMSO-$d_6$, TMS internal standard)

δ: 1.66–1.78 (2H, m), 1.84–1.94 (1H, m), 2.02–2.08 (1H, m), 2.40–2.44 (1H, m), 3.06–3.24 (5H, m), 3.52–3.60 (1H, m), 3.98–4.04 (1H, m), 4.72 (1H, d, J=14 Hz), 4.77 (1H, d, J=14 Hz), 7.45–7.52 (2H, m), 7.68–7.72 (2H, m), 7.91–7.92 (1H, m), 8.19–8.22 (2H, m), 10.08 (1H, brs).

Example 21
3-(9H-Xanthen-9-on-1-ylmethoxy)quinuclidine hydrochloride

Material compound: borane-[3-(9H-xanthen-9-on-1-ylmethoxy)quinuclidine] complex

Melting point: 245°–247° C.

Nuclear magnetic resonance spectrum (DMSO-$d_6$, TMS internal standard)

δ: 1.70–1.81 (2H, m), 1.91–1.98 (1H, m), 2.04–2.13 (1H, m), 2.45–2.47 (1H, m), 3.13–3.28 (5H, m), 3.59–3.65 (1H, m), 4.06–4.13 (1H, m), 5.24 (2H, s), 7.46–7.50 (1H, m), 7.61–7.70 (3H, m), 7.85–7.90 (2H, m).

Example 22
(Z)-3-[2-(9H-Xanthen-9-on-2-ylmethoxy)ethylidene]quinuclidine hydrochloride Material compound: borane-[(Z)-3-[2-(9H-xanthen-9-on-2-ylmethoxy)ethylidene]quinuclidine] complex Melting point: 199°–202° C.

Nuclear magnetic resonance spectrum (DMSO-$d_6$, TMS internal standard)

δ: 1.76–1.86 (2H, m), 1.92–1.98 (2H, m), 2.64 (1H, s), 3.20–3.29 (4H, m), 3.98 (2H, s), 4.02 (2H, d, J=6 Hz), 4.63 (2H, s), 5.59–5.62 (1H, m), 7.48–7.52 (1H, m), 7.68–7.70 (2H, m), 7.84–7.91 (2H, in), 8.16 (1H, s), 8.21 (1H, d, J=8 Hz), 10.67 (1H, brs).

Example 23
3-(10-Ethylphenothiazin-3-ylmethoxy)quinuclidine

At 0° C., a hydrogen chloride ethanol solution (ca. 5M, 1 ml) was added to a mixture of borane-[3-(10-ethylphenothiazin-3-ylmethoxy)quinuclidine] complex (1.28 g, 3.37 mmol) and acetone (5 ml), and the mixture was stirred for 30 minutes. Triethylamine (2 ml) was added to the reaction mixture, and the mixture was concentrated under a reduced pressure. Chloroform and a 2N sodium hydroxide aqueous solution (each 30 ml) were added to the resulting residue in that order, and then the reaction product was extracted with chloroform. The extract was dried over anhydrous magnesium sulfate and then concentrated under a reduced pressure. The resulting residue was purified by silica gel column chromatography (eluent; 29% aqueous ammonia:methanol:chloroform=0.3:3:97) to give the title compound (900 mg, 2.46 mmol, 73%) as yellow oil.

Mass spectrometry data (m/z): 366 (M$^+$) (GC)

Nuclear magnetic resonance spectrum (CDCl$_3$, TMS internal standard)

δ: 1.36–1.44 (5H, m), 1.66–1.72 (1H, m), 1.89–2.06 (2H, m), 2.66–2.82 (4H, m), 2.91–2.96 (1H, m), 3.06–3.11 (1H, m), 3.53–3.55 (1H, m), 3.92 (2H, q, J=7 Hz), 4.32 (1H, d, J=12 Hz), 4.42 (1H, d, J=12 Hz), 6.82–6.91 (3H, m), 7.10–7.15 (4H, m).

The following compounds of Examples 24 to 28 were obtained in the same manner as Example 23.

Example 24
3-(10-Butylphenothiazin-3-ylmethoxy)quinuclidine

Material compound: borane-[3-(10-butylphenothiazin-3-ylmethoxy)quinuclidine] complex Mass spectrometry data (m/z): 394 (M$^+$) (GC)

Nuclear magnetic resonance spectrum (CDCl$_3$, TMS internal standard)

δ: 0.93 (3H, t, J=7 Hz), 1.37–1.49 (4H, m), 1.67–1.81 (3H, m), 1.90–1.98 (1H, m), 2.06–2.07 (1H, m), 2.70–2.83 (4H, m), 2.92–2.95 (1H, m), 3.08–3.12 (1H, m), 3.54–3.56 (1H, m), 3.84 (2H, t, J=7 Hz), 4.33 (1H, d, J=12 Hz), 4.42 (1H, d, J=12 Hz), 6.81–6.91 (3H, m), 7.10–7.15 (4H, m).

Example 25
3-[10-(1-Methylethyl)phenothiazin-3-ylmethoxy]quinuclidine

Material compound: borane-[3-[10-(1-methylethyl)phenothiazin-3-ylmethoxy]quinuclidine] complex Mass spectrometry data (m/z): 380 (M$^+$) (GC)

Nuclear magnetic resonance spectrum (CDCl$_3$, TMS internal standard)

δ: 1.34–1.48 (2H, m), 1.62 (6H, d, J=7 Hz), 1.66–1.76 (1H, m), 2.06–2.10 (1H, m), 2.70–2.86 (4H, m), 2.94–3.00 (1H, m), 3.10–3.16 (1H, m), 3.35–3.57 (1H, m), 4.24–4.30 (1H, m), 4.33 (1H, d, J=12 Hz), 4.43 (1H, d, J=12 Hz), 6.89–6.92 (1H, m), 7.00–7.04 (2H, m), 7.08–7.14 (4H, m)

Example 26
10-Methyl-3-(3-quinuclidinyloxymethyl)phenothiazine-5-oxide

Material compound: borane-[10-methyl-3-(3-quinuclidinyloxymethyl)phenothiazine-5-oxide] complex Melting point: 164°–166° C.

Nuclear magnetic resonance spectrum (CDCl$_3$, TMS internal standard)

δ: 1.35–1.45 (2H, m), 1.70 (1H, m), 1.91 (1H, m), 2.09 (1H, m), 2.69 (1H, m), 2.70–2.80 (2H, m), 2.93 (1H, m), 3.11 (1H, m), 3.77 (3H, s), 4.51 (1H, m), 4.61 (1H, m), 7.25 (1H, m), 7.35–7.40 (2H, m), 7.60–7.65 (2H, m), 7.90–7.95 (2H, m).

Example 27
3-(3-Chloro-10-methylphenoxazin-7-ylmethoxy)quinuclidine

Material compound: borane-[3-(3-chloro-10-methylphenoxazin-7-ylmethoxy)quinuclidine] complex Melting point: 89°–90° C.

Nuclear magnetic resonance spectrum (CDCl$_3$, TMS internal standard)

δ: 1.44–1.50 (2H, m), 1.70–1.75 (1H, m), 1.92–1.98 (1H, m), 2.06–2.10 (1H, m), 2.72–2.86 (4H, m), 2.94–3.06 (4H, m), 3.10–3.15 (1H, m), 3.56–3.58 (1H, m), 4.28 (1H, d, J=12 Hz), 4.37 (1H, d, J=12 Hz), 6.40 (1H, d, J=8 Hz), 6.48 (1H, d, J=8 Hz), 6.69 (2H, s), 6.79–6.82 (2H, m).

Example 28
(Z)-3-[2-(10-Methylphenothiazin-3-ylmethoxy)ethylidene]quinuclidine Material compound: borane-[(Z)-3-[2-(10-methylphenothiazin-3-ylmethoxy)ethylidene]quinuclidine] complex Mass spectrometry data (m/z): 379 (M$^+$) (FAB)

Nuclear magnetic resonance spectrum (CDCl$_3$, TMS internal standard)

δ: 1.70–1.74 (4H, m), 2.35–2.36 (1H, m), 2.80–2.94 (4H, m), 3.37 (3H, s), 3.47 (2H, s), 3.90 (2H, d, J=6 Hz), 4.40 (2H, s), 5.34–5.37 (1H, m), 6.77–6.81 (2H, m), 6.90–6.93 (1H, m), 7.13–7.17 (4H, m).

Example 29
3-[(10-Methylphenothiazin-3-ylmethyl)amino]quinuclidine difumarate At 0° C., sodium triacetoxy borohydride (1.24 g, 5.85 mmol) was added to a mixture of 3-aminoquinuclidine (405 mg, 3.21 mmol), 3-formyl-10-methylphenothiazine (704 mg, 2.92 mmol), acetic acid (1.8 ml) and methylene chloride (29 ml), and the mixture was stirred for 1 hour. A saturated sodium bicarbonate aqueous solution (30 ml) was added to the reaction mixture and the reaction product was extracted with chloroform. The extract was washed with saturated sodium chloride aqueous solution, dried over anhydrous magnesium sulfate, and then concentrated under a reduced pressure to give a colorless foamy material (1.23 g). To a mixture thereof with ethanol (25 ml) was added fumaric acid (817 mg, 5.85 mmol), and the resulting precipitate was collected by filtration to give the title compound (1.41 g, 2.42 mmol, 83%) as yellow crystals.

Melting point: 182°–184° C.

Nuclear magnetic resonance spectrum (DMSO-$d_6$, TMS internal standard)

δ: 1.54–1.66 (2H, m), 1.78–1.86 (1H, m), 2.06–2.12 (2H, m), 2.75 (1H, d, J=13 Hz), 2.94–3.18 (6H, m), 3.30 (3H, s), 3.33–3.37 (1H, m), 3.57–3.66 (2H, m), 6.54 (4H, s), 6.89–6.96 (3H, m), 7.15–7.23 (4H, m)

Example 30

3-Hydroxy-3-[2-(10-methylphenothiazin-3-yl)ethyl]quinuclidine

In an atmosphere of argon, a hexane solution of n-butyl lithium (1.65M, 10.1 ml, 16.7 mmol) was added at −78° C. to a THF (25 ml) solution of 3-(2,2-dibromovinyl)-10-methylphenothiazine (3.13 g, 7.94 mmol), and the mixture was stirred for 1 hour and then at room temperature for 1 hour. The reaction mixture was again cooled at −78° C., and a THF (8 ml) solution of 3-quinuclidinone (1.09 g, 8.70 mmol) was added dropwise. The mixture was stirred at −78° C. for 1 hour and then with ice-cooling for 30 minutes. Water (5 ml) was added to the reaction mixture and the mixture was concentrated under a reduced pressure. A potassium carbonate aqueous solution was added and the reaction product was extracted with chloroform which was heated at about 50° C. The extract was dried over anhydrous magnesium sulfate and then concentrated under a reduced pressure. The resulting residue was recrystallized from ethanol-chloroform to give the title compound (1.75 g, 4.83 mmol, 61%) as yellow crystals.

Melting point: 210°–213° C.

Nuclear magnetic resonance spectrum (DMSO-$d_6$, TMS internal standard)

δ: 1.28 (1H, m), 1.55 (1H, m), 1.80–1.95 (3H, m), 2.65–2.70 (4H, m), 2.81 (1H, d), 3.04 (1H, d), 3.31 (1H, s), 5.53 (1H, s), 6.91 (l1H, d), 6.95–6.70 (2H, m), 7.15–7.25 (4H, m).

Example 31

3-Hydroxy-3-quinuclidinylmethyl 10-methyl-2-phenothiazinyl ketone

In an atmosphere of argon, a hexane solution of n-butyl lithium (1.71M, 4.94 ml, 8.45 mmol) was added at −78° C. to a THF (8 ml) solution of diisopropylamine (1.23 ml, 8.8 mmol), and the mixture was stirred for 40 minutes. To the solution of the resulting lithium diisopropylamide was added a THF (8 ml) solution of 2-acetyl-10-methylphenothiazine (1.96 g, 7.68 mmol), and the mixture was stirred for 1 hour. A THF (8 ml) solution of 3-quinuclidinone (951 mg, 7.60 mmol) was added, the mixture was stirred at −78° C. for 30 minutes and then with ice-cooling for 15 minutes. Water was added to the reaction mixture and the reaction product was extracted with chloroform. The extract was washed with saturated sodium chloride aqueous solution, dried over anhydrous magnesium sulfate, and then concentrated under a reduced pressure. The resulting residue was purified by silica gel column chromatography (eluent; 29% aqueous ammonia:methanol:chloroform=1:10:90) to give the title compound (1.55 g, 4.07 mmol, 53%) as yellow foam.

Mass spectrometry data (m/z): 380 (M⁺)

Nuclear magnetic resonance spectrum (CDCl$_3$, TMS internal standard)

δ: 1.34 (1H, m), 1.55–1.60 (2H, m), 1.95 (1H, m), 2.17 (1H, m), 2.70–2.85 (4H, m), 2.95–3.05 (2H, m), 3.19 (1H, d), 3.36 (1H, d), 3.42 (3H, s), 4.13 (1H, s), 6.82 (1H, d), 6.95 (1H, m), 7.10 (1H, m), 7.15–7.25 (2H, m), 7.34 (1H, s), 7.48 (1H, s).

Example 32

3-Hydroxy-3-quinuclidinylmethyl 2-phenothiazinyl ketone

In an atmosphere of argon, a hexane solution of n-butyl lithium (1.71M, 6.1 ml, 10.5 mmol) was added at −78° C. to a THF (10 ml) solution of diisopropylamine (1.54 ml, 11 mmol), and the mixture was stirred for 40 minutes. To the resulting solution of lithium diisopropylamide was added a THF (8 ml) solution of 2-acetylphenothiazine (1.21 g, 5.0 mmol). The mixture was stirred for 30 minutes, a THF (3 ml) solution of 3-quinuclidinone (626 mg, 5.0 mmol) was added, and the mixture was stirred for 30 minutes. Water was added to the reaction mixture and the reaction product was extracted with chloroform. The extract was washed with saturated sodium chloride aqueous solution, dried over anhydrous magnesium sulfate, and then concentrated under a reduced pressure. The resulting residue was purified by silica gel column chromatography (eluent; 29% aqueous ammonia:methanol:chloroform=0.8:8:92 then 2:20:80), to give the title compound (127 mg, 0.35 mmol, 7%) as yellow foam.

Melting point: 169°–171° C.

Nuclear magnetic resonance spectrum (CDCl$_3$, TMS internal standard)

δ: 1.39 (1H, m), 1.60–1.65 (2H, m), 1.98 (1H, m), 2.22 (1H, m), 2.80–3.30 (8H, m), 4.18 (1H, brs), 6.13 (1H, brs), 6.56 (1H, d), 6.83 (1H, dd), 6.92 (1H, d), 6.95–7.00 (2H, m), 7.10 (1H, s), 7.32 (1H, d).

The following compound of Example 33 was obtained in the same manner as Example 1.

Example 33

(Z)-3-[2-(Carbazol-2-yloxy)-1-fluoroethylidene]quinuclidine hydrochloride

Material compound: borane-[(Z)-3-(1-fluoro-2-hydroxyethylidene)quinuclidine] complex Melting point: 246°–249° C.

Nuclear magnetic resonance spectrum (DMSO-$d_6$, TMS internal standard)

δ: 1.76–1.82 (2H, m), 1.96–2.02 (2H, m), 3.10–3.11 (1H, m), 3.22–3.33 (4H, m), 4.07 (2H, s), 4.89 (2H, d, J=22 Hz), 6.82 (1H, dd, J=3, 9 Hz), 7.04 (1H, d, J=3 Hz), 7.10–7.13 (1H, m), 7.28–7.31 (1H, m), 7.43 (1H, d, J=8 Hz), 7.98–8.01 (2H, m), 10.76 (1H, s), 11.22 (1H, s).

The following compounds of Examples 34 and 35 were obtained in the same manner as in Example 13.

Example 34

3-(9H-Xanthen-9-on)-4-ylmethoxy)quinuclidine hydrochloride

Material compounds: 4-bromomethyl-9H-xanthen-9-one, borane-(3-quinuclidinol) complex Melting point: 226°–229° C.

Nuclear magnetic resonance spectrum (DMSO-$d_6$, TMS internal standard)

δ: 1.71–1.79 (2H, m), 1.92–1.98 (1H, m), 2.08–2.12 (1H, m), 3.08–3.21 (6H, m), 3.56–3.62 (1H, m), 4.88 (1H, d, J=12 Hz), 7.72 (1H, d, J=9 Hz), 7.90–7.97 (2H, m), 8.17–8.23 (2H, m), 10.47 (1H, s).

Example 35

(Z)-3-[2-(9H-Xanthen-9-on-2-yloxy)ethylidene]quinuclidine hydrochloride

Material compounds: 2-hydroxy-9H-xanthen-9-one, borane-[(Z)-3-(2-hydroxyethylidene)quinuclidine] complex Melting point: 257°–260° C.

Nuclear magnetic resonance spectrum (DMSO-$d_6$, TMS internal standard)

δ: 1.83 (2H, m), 1.99 (2H, m), 2.72 (1H, m), 3.20–3.35 (4H, m), 4.15 (2H, s), 4.67 (2H, d), 5.74 (1H, m), 7.45–7.55 (2H, m), 7.61 (1H, d), 7.65–7.70 (2H, m), 7.89 (1H, m), 8.21 (1H, dd), 10.77 (1H, brs).

Chemical structures of the compounds obtained in Examples 1 to 35 are shown in Table 3.

TABLE 3

| Example | Chemical Structural Formula |
|---|---|
| 1 | |
| 2 | |
| 3 | |
| 4 | |
| 5 | |
| 6 | |
| 7 | |
| 8 | |
| 9 | |

TABLE 3-continued

| Example | Chemical Structural Formula |
|---|---|
| 10 | |
| 11 | |
| 12 | |
| 13 | |
| 14 | |
| 15 | |
| 16 | |
| 17 | |

TABLE 3-continued
| Example | Chemical Structural Formula |
|---------|------------------------------|
| 18 | 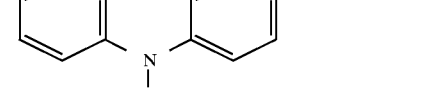 |
| 19 |  |
| 20 | 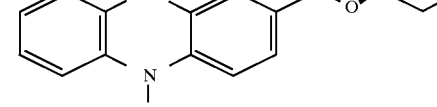 |
| 21 |  |
| 22 | 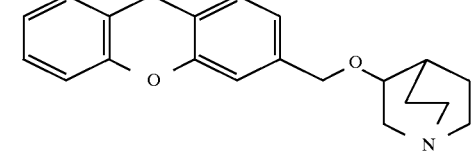 |
| 23 |  |
| 24 | 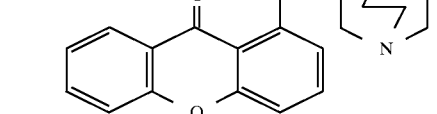 |

TABLE 3-continued

| Example | Chemical Structural Formula |
| --- | --- |
| 25 | |
| 26 | |
| 27 | |
| 28 | |
| 29 | |
| 30 | |
| 31 | |

TABLE 3-continued

| Example | Chemical Structural Formula |
|---|---|
| 32 | |
| 33 | |
| 34 | |
| 35 | |

We claim:

1. A quinuclidine derivative having a tricyclic hetero condensed ring, represented by the following formula (I), a salt thereof, a hydrate thereof or a solvate thereof;

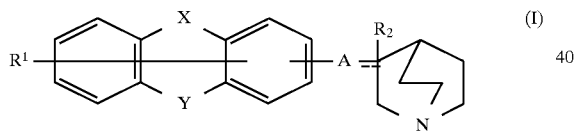

wherein
- $R_1$: a hydrogen atom, a halogen atom or a lower alkyl group,
- $R_2$: a hydrogen atom, a hydroxyl group or a lower alkoxy group,
- ...: a single bond or a double bond, with the proviso that $R_2$ does not exist when ... is a double bond,
- X and Y: the same or different from each other and each represents a bond, an oxygen atom (—O—), a carbonyl group (—CO—), a group represented by the formula —S(O)$_p$— or a group represented by the formula —NR$_3$—,
- p: 0, 1 or 2,
- $R_3$: a hydrogen atom or a lower alkyl group which may have a substituent,
- A: a saturated or unsaturated lower alkylene group, a group represented by the formula —(CH$_2$)$_m$Z(CH$_2$)$_n$— or a group represented by the formula —(CH$_2$)$_m$Z(CH$_2$)$_n$CR$_4$=,
  - Z: an oxygen atom (—O—), a group represented by the formula —S(O)$_q$—, a carbonyl group (—CO—) or a group represented by the formula —NR$_5$—,
- $R_4$: a hydrogen atom, a halogen atom or a lower alkyl group,
- $R_5$: a hydrogen atom or a lower alkyl group,
- m and n: the same or different from each other and each is 0 or an integer of 1 to 5,
- m+n: an integer of 1 to 5, and
- q: 0, 1 or 2,
- with the proviso that A is a group represented by the formula —(CH$_2$)$_m$Z(C$_2$)$_n$CR$_4$= when either one of X and Y is a bond.

2. The compound according to claim 1, wherein A is an unsaturated lower alkylene group, a group represented by the formula —(CH$_2$)$_m$Z(CH$_2$)$_n$— or a group represented by the formula —(CH$_2$)$_m$Z(CH$_2$)$_n$CR$_4$= and Z is an oxygen atom (—O—), a carbonyl group (—CO—) or a group represented by the formula —NR$_5$—.

3. The compound according to claim 2, wherein the tricyclic group represented by

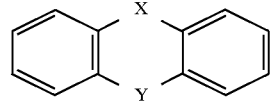

in the formula (I) is

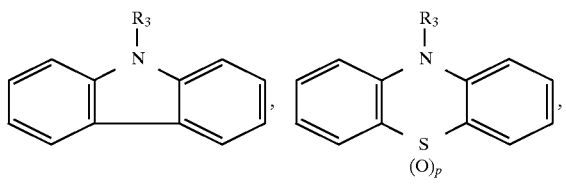

-continued

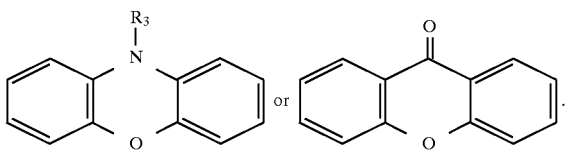

4. The compound according to claim 3, wherein $R_3$ is a hydrogen atom or a lower alkyl group which may have a hydroxyl group, a lower alkoxy group, an amino group, a mono- or di-lower alkylamino group, a carboxyl group, a lower alkoxycarbonyl group, a carbamoyl group, a mono- or di-lower alkylcarbamoyl group or an aryl group as its substituent.

5. The compound according to claim 4, wherein A is a group represented by the formula $-(CH_2)_m Z(CH_2)_n CR_4=$.

6. The compound according to claim 4, wherein A is a group represented by the formula $-(C_2)_m O(C_2)_n CR_4=$.

7. The compound according to claim 1 which is (Z)-3-[2-(Carbazol-2-yloxy)ethylidene]quinuclidine, a salt thereof, a hydrate thereof or a solvate thereof.

8. (Z)-3-[2-(Carbazol-2-yloxy)-1-methylethylidene]quinuclidine, a salt thereof, a hydrate thereof or a solvate thereof.

9. (E)-3-[2-(Carbazol-2-yloxy)-1-fluoroethylidene]quinuclidine, a salt thereof, a hydrate thereof or a solvate thereof.

10. A pharmaceutical composition which comprises a pharmaceutically acceptable carrier and the compound of any one of claims 1 to 9 or a pharmaceutically acceptable salt thereof as its active ingredient.

11. A method for selectively inhibiting squalene synthase activity in a patient which comprises administering to the patient a therapeutically effective amount of the pharmaceutical composition of claim 10.

12. The method of claim 11 wherein the compound is (z)-3-[2-(Carbazol-2-yloxy)ethylidene]quinuclidine, a salt thereof, a hydrate thereof or a solvate thereof.

13. The method of claim 11 wherein the compound is (z)-3-[2-(Carbazol-2-yloxy)-1-methylethylidene]quinuclidine, a salt thereof, a hydrate thereof or a solvate thereof.

14. The method of claim 11 wherein the compound is (E)-3-[2-(Carbazol-2-yloxy)-1-fluoroethylidene]quinuclidine, a salt thereof, a hydrate thereof or a solvate thereof.

15. The method of claim 11 wherein the pharmaceutical composition is effective as a cholesterol lowering agent.

16. The method of claim 11 wherein the pharmaceutical composition is effective in the prevention or treatment of hyperlipemia.

17. The method of claim 11 wherein the pharmaceutical composition is effective in the prevention or treatment of arteriosclerosis, aneurysm, ischemic heart disease or cerebral arteriosclerotic disease.

18. The method of claim 17 wherein the ischemic heart disease is myocardial infarction or angina pectoris.

19. The method of claim 17 wherein the cerebral arteriosclerotic disease is cerebral infarction.

* * * * *